United States Patent
Italiano et al.

(10) Patent No.: US 10,710,073 B2
(45) Date of Patent: *Jul. 14, 2020

(54) SYSTEM AND METHOD FOR BIOMIMETIC FLUID PROCESSING

(71) Applicants: The Brigham and Women's Hospital, Inc., Boston, MA (US); President and Fellows of Harvard College, Cambridge, MA (US); Vilnius University, Vilnius (LT)

(72) Inventors: Joseph Italiano, Chestnut Hill, MA (US); Linas Mazutis, Boston, MA (US); Jonathan N. Thon, Cambridge, MA (US); David A. Weitz, Boston, MA (US)

(73) Assignees: Brigham and Women's Hospital, Inc., Boston, MA (US); President and Fellows of Harvard College, Cambridge, MA (US); Vilnius University, Vilnius (LT)

( * ) Notice: Subject to any disclaimer, the term of this patent is extended or adjusted under 35 U.S.C. 154(b) by 0 days.

This patent is subject to a terminal disclaimer.

(21) Appl. No.: 16/422,030

(22) Filed: May 24, 2019

(65) Prior Publication Data

US 2019/0283027 A1 Sep. 19, 2019

Related U.S. Application Data

(63) Continuation of application No. 15/709,989, filed on Sep. 20, 2017, now Pat. No. 10,343,163, which is a
(Continued)

(51) Int. Cl.
*B01L 3/00* (2006.01)
*C12M 1/00* (2006.01)
(Continued)

(52) U.S. Cl.
CPC ... *B01L 3/502753* (2013.01); *B01L 3/502746* (2013.01); *B01L 3/502776* (2013.01);
(Continued)

(58) Field of Classification Search
CPC ..... B01L 2200/0647; B01L 2200/0668; B01L 2300/0681; B01L 2300/0816;
(Continued)

(56) References Cited

U.S. PATENT DOCUMENTS 7,718,420 B2    5/2010  Kim
9,795,965 B2   10/2017  Italiano
(Continued)

FOREIGN PATENT DOCUMENTS

CN       2726112     9/2005
CN     102058399     5/2011
(Continued)

OTHER PUBLICATIONS

European Search Report and Written Opinion for Application EP13870350, dated Sep. 5, 2016, 6 pages.
(Continued)

*Primary Examiner* — Maureen Wallenhorst
(74) *Attorney, Agent, or Firm* — Quarles & Brady LLP

(57) ABSTRACT

A system and method are provided for harvesting target biological substances. The system includes a substrate and a first and second channel formed in the substrate. The channels longitudinally extending substantially parallel to each other. A series of gaps extend from the first channel to the second channel to create a fluid communication path passing between a series of columns with the columns being longitudinally separated by a predetermined separation distance. The system also includes a first source configured to selectively introduce into the first channel a first biological composition at a first channel flow rate and a second source
(Continued)

configured to selectively introduce into the second channel a second biological composition at a second channel flow rate. The sources are configured to create a differential between the first and second channel flow rates to generate physiological shear rates along the second channel that are bounded within a predetermined range.

20 Claims, 21 Drawing Sheets

Related U.S. Application Data continuation of application No. 14/758,915, filed as application No. PCT/US2013/070910 on Nov. 20, 2013, now Pat. No. 9,795,965.

(60) Provisional application No. 61/848,424, filed on Jan. 3, 2013.

(51) Int. Cl.
| | |
|---|---|
| C12M 1/12 | (2006.01) |
| C12M 1/34 | (2006.01) |
| C12M 3/06 | (2006.01) |
| G01N 33/86 | (2006.01) |
| G01N 33/49 | (2006.01) |

(52) U.S. Cl.
CPC .......... *C12M 23/16* (2013.01); *C12M 23/20* (2013.01); *C12M 25/02* (2013.01); *C12M 29/04* (2013.01); *C12M 29/10* (2013.01); *C12M 29/20* (2013.01); *C12M 41/36* (2013.01); *C12M 41/40* (2013.01); *G01N 33/86* (2013.01); *B01L 2200/0647* (2013.01); *B01L 2200/0668* (2013.01); *B01L 2300/0681* (2013.01); *B01L 2300/0816* (2013.01); *B01L 2400/086* (2013.01); *G01N 33/491* (2013.01); *G01N 2800/222* (2013.01); *Y10T 436/25375* (2015.01)

(58) Field of Classification Search
CPC ......... B01L 2400/086; B01L 3/502746; B01L 3/502753; B01L 3/502776; C12M 23/16; C12M 23/20; C12M 25/02; C12M 29/04; C12M 29/10; C12M 29/20; C12M 41/36; C12M 41/40; G01N 2800/222; G01N 33/48; G01N 33/49; G01N 33/491; G01N 33/4915; G01N 33/86; Y10T 436/25; Y10T 436/25375; Y10T 436/2575

USPC .... 436/10, 63, 174, 177, 180; 422/502, 503, 422/504, 505, 534, 73; 435/29, 30, 435/287.3, 289.1, 297.2, 395

See application file for complete search history.

(56) References Cited

U.S. PATENT DOCUMENTS

| | | | |
|---|---|---|---|
| 10,343,163 B2* | 7/2019 | Italiano | C12M 23/16 |
| 2005/0009101 A1 | 1/2005 | Blackburn | |
| 2005/0069459 A1 | 3/2005 | Ahn | |
| 2005/0112184 A1 | 5/2005 | Jahn | |
| 2006/0154361 A1 | 7/2006 | Wikswo | |
| 2007/0243608 A1 | 10/2007 | Kyba | |
| 2010/0009430 A1 | 1/2010 | Wan | |
| 2010/0041128 A1 | 2/2010 | Banes | |
| 2011/0000823 A1 | 1/2011 | Hamad | |
| 2011/0039285 A1 | 2/2011 | Sadaba Champetier De Ribes | |
| 2012/0238020 A1 | 9/2012 | Baruch | |
| 2013/0295601 A1 | 11/2013 | Park | |
| 2016/0002586 A1 | 1/2016 | Mitchell | |
| 2016/0272941 A1 | 9/2016 | Baruch | |
| 2018/0334652 A1* | 11/2018 | Thon | C12N 5/0644 |

FOREIGN PATENT DOCUMENTS

| | | |
|---|---|---|
| CN | 102698672 | 10/2012 |
| RU | 2076742 | 4/1997 |
| RU | 2392314 | 6/2010 |
| WO | 2006001954 | 1/2006 |
| WO | 2010063823 | 6/2010 |
| WO | 2010123594 | 10/2010 |
| WO | 2011002745 | 1/2011 |
| WO | 2012118799 | 9/2012 |
| WO | 2013013220 | 1/2013 |

OTHER PUBLICATIONS

Nakagawa, et al., Two Differential Flows in a Bioreactor Promoted Platelet Generation from Human Pluripotent Stem Cell-Derived Megakaryocytes, Experimental Hematology, 2013, 41:742-748.
PCT International Search Report, PCT/US2013/070910, dated Mar. 20, 2014.
Synnevag, J. F. et al. "Adaptive beamforming applied to medical ultrasound imaging." IEEE transactions on ultrasonics, ferroelectrics, and frequency control 54.8 (2007): 1606-1613.

* cited by examiner

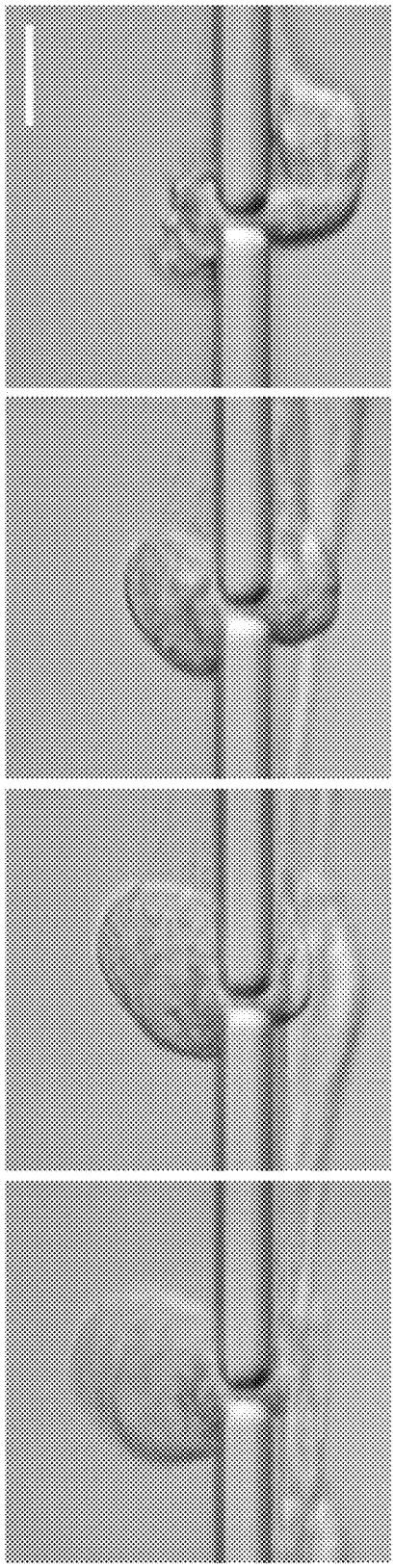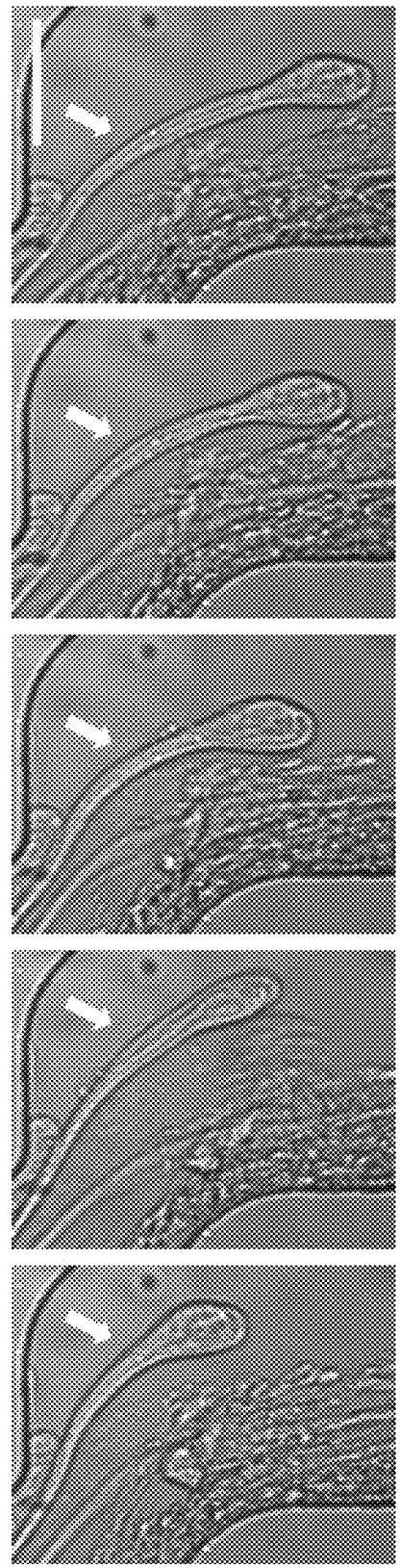
FIG. 4A
FIG. 4B

FIG. 4F
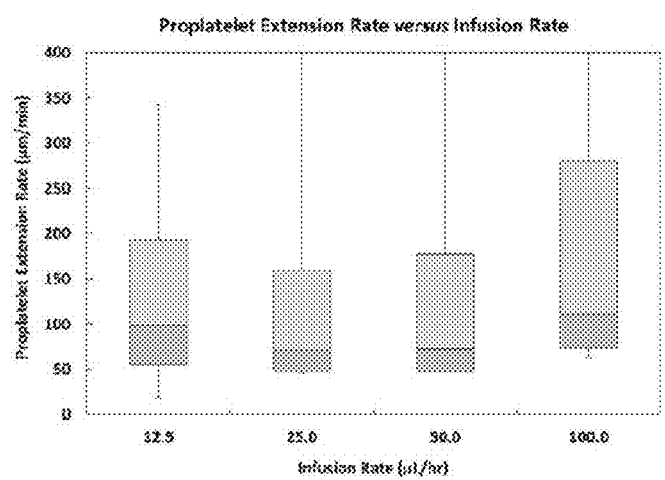
FIG. 4G
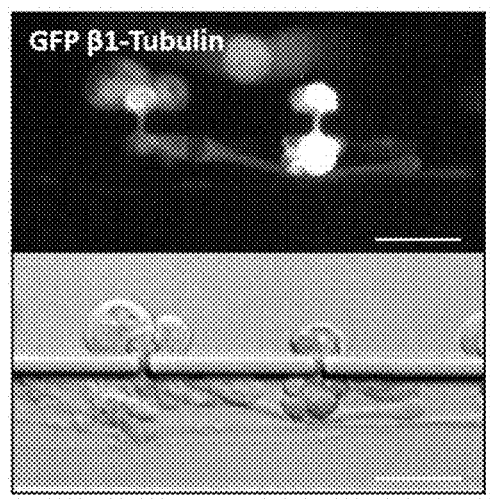
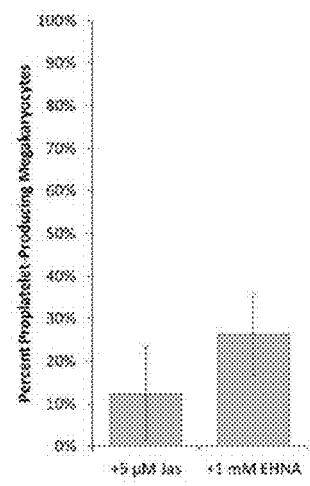
FIG. 4H
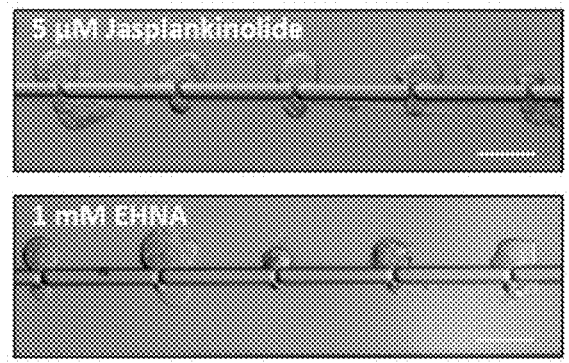
FIG. 4I

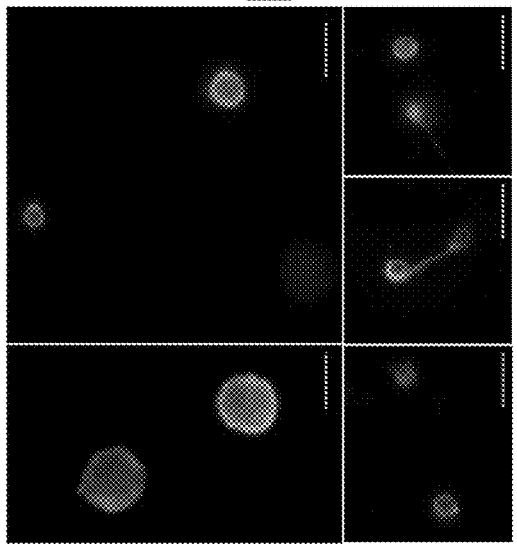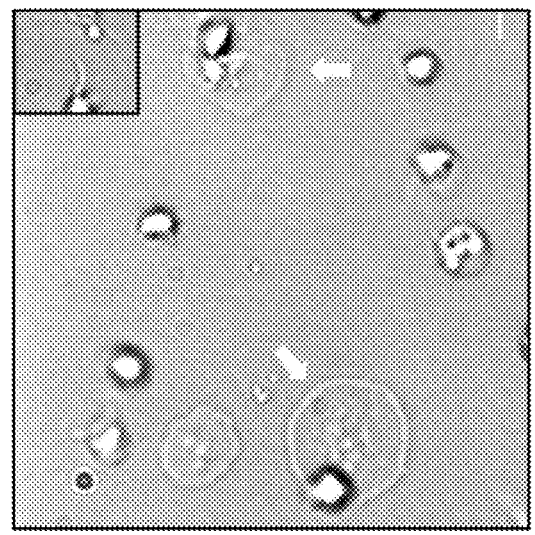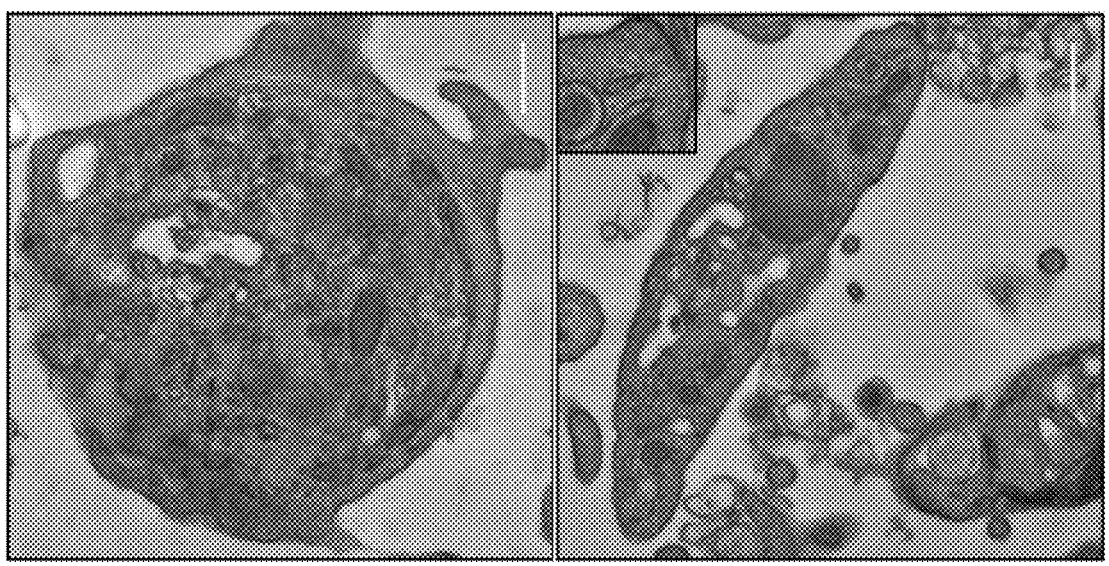

SYSTEM AND METHOD FOR BIOMIMETIC FLUID PROCESSING

CROSS-REFERENCE TO RELATED APPLICATIONS

This application is a continuation of U.S. patent application Ser. No. 15/709,989, now U.S. Pat. No. 10,343,163, filed Sep. 20, 2017, which is a continuation of U.S. patent application Ser. No. 14/758,915 filed Jul. 1, 2015, now U.S. Pat. No. 9,795,965, which is the U.S. National Stage Application of International Patent Application PCT/US2013/070910 filed Nov. 20, 2013, which claims the benefit of, and incorporates herein by reference in its entirety, U.S. Provisional Patent Application 61/848,424 filed Jan. 3, 2013.

STATEMENT REGARDING FEDERALLY SPONSORED RESEARCH

This invention was made with government support under 1K99HL114719-01A1 awarded by the National Institutes of Health. The government has certain rights in the invention.

BACKGROUND OF THE INVENTION

The present disclosure generally relates to fluid systems, including microfluidic devices, systems that include such devices, and methods that use such devices and systems. More particularly, the present disclosure relates to devices, systems, and methods for generating functional biological material, substances, or agents based on biomimetic platforms.

Blood platelets (PLTs) are essential for hemostasis, angiogenesis, and innate immunity, and when numbers dip to low levels, a condition known as thrombocytopenia, a patient is at serious risk of death from hemorrhage. Some causes for low platelet count include surgery, cancer, cancer treatments, aplastic anemia, toxic chemicals, alcohol, viruses, infection, pregnancy, and idiopathic immune thrombocytopenia.

Replacement PLTs to treat such conditions are generally derived entirely from human donors, despite serious clinical concerns owing to their immunogenicity and associated risk of sepsis. However, the shortages created by increased demand for PLT transfusions, coupled with near-static pool of donors and short shelf-life on account of bacterial testing and deterioration, are making it harder for health care professionals to provide adequate care for their patients. Moreover, alternatives such as artificial platelet substitutes, have thus far failed to replace physiological platelet products.

In vivo, PLTs are produced by progenitor cells, known as megakaryocytes (MKs). Located outside blood vessels in the bone marrow (BM), MKs extend long, branching cellular structures (proPLTs) into sinusoidal blood vessels, where they experience shear rates and release PLTs into the circulation. While functional human PLTs have been grown in vitro, cell culture approaches to-date have yielded only about 10 percent proPLT production and 10-100 PLTs per human MK. By contrast, nearly all adult MKs in humans must produce roughly 1,000-10,000 PLTs each to account for the number of circulating PLTs. This constitutes a significant bottleneck in the ex vivo production of platelet transfusion unit. Although second generation cell culture approaches have provided further insight into the physiological drivers of PLT release, they have been unable to recreate the entire BM microenvironment, exhibiting limited individual control of extracellular matrix (ECM) composition, BM stiffness, endothelial cell contacts, or vascular shear rates; and have been unsuccessful in synchronizing proPLT production, resulting in non-uniform PLT release over a period of 6-8 days. Moreover, the inability to resolve proPLT extension and release under physiologically relevant conditions by high-resolution live-cell microscopy has significantly hampered efforts to identify the cytoskeletal mechanics of PLT production to enable drug development and establish new treatments for thrombocytopenia. Therefore, an efficient, donor-independent PLT system capable of generating clinically significant numbers of functional human PLTs is necessary to obviate risks associated with PLT procurement and storage, and help meet growing transfusion needs.

Considering the above, there continues to be a clear need for devices, systems, and methods employing platforms that can recapitulate vascular physiology to accurately reflect the processes, mechanisms, and conditions influencing the efficient production of functional human blood platelets. Such platforms would prove highly useful for the purposes of efficiently generating human platelets for infusion, as well as for establishing drug effects and interactions in the preclinical stages of development.

SUMMARY OF THE INVENTION

The present invention overcomes the aforementioned drawbacks by providing a biomimetic fluidic system and method, for example, for generating functional human blood platelets using a platform representative of physiologically accurate conditions, environments, structures, and dynamic flows. The approach is amenable for infusive treatment of platelet-deficient conditions, such as thrombocytopenia, as well as for drug development applications.

In accordance with one aspect of the present invention, a biomimetic microfluidic system is provided that includes a substrate. The system also includes a first channel formed in the substrate that extends from a first input to a first output and along a longitudinal dimension and extends along a first transverse dimension. The system also includes a second channel formed in the substrate that extends from a second input to a second output along the longitudinal dimension and extends along a second transverse dimension. The first and second channels extend substantially parallel. The system further includes a series of gaps extending from the first channel to the second channel to create a fluid communication path passing between a series of columns. The columns are longitudinally separated by a predetermined separation distance. Notably, the predetermined distance may be uniform or may vary within a range of predetermined distances such that the gaps have varying widths. The system also includes a first source connected to the first input and configured to selectively introduce into the first channel at least one first biological composition at a first channel flow rate. The system next includes a second source connected to the second input and configured to selectively introduce into the second channel at least one second biological composition at a second channel flow rate. The first channel flow rate and the second channel flow rate create a differential configured to generate physiological shear rates along the second channel bounded within a predetermined range and to influence the flow within the first channel through the series of gaps.

In another aspect of the present invention, a method is disclosed for producing a physical model of at least one of a bone marrow and blood vessel structure. The method includes providing a biomimetic microfluidic system that includes a substrate and a first channel formed in the substrate that extends from a first input to a first output along a longitudinal dimension and extends along a first transverse dimension. The system also includes a second channel formed in the substrate that extends from a second input to a second output along the longitudinal dimension and extends along a second transverse dimension. The first and second channels extend substantially parallel. The system further includes a series of gaps extending from the first channel to the second channel to create a fluid communication path passing between a series of columns. The columns are longitudinally separated by a predetermined separation distance. The system also includes a first source connected to the first input and a second source connected to the second input. The method includes introducing the first biological substance into the upper channel at a first channel flow rate using the first source and introducing the second biological substance into the lower channel at a second channel flow rate using the second source to create a differential between the first and second channel flow rates to generate physiological shear rates along the second channel that are bounded within a predetermined range. The method also includes harvesting a target biological substance produced proximate to the gaps by the physiological shear rates.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The present invention will hereafter be described with reference to the accompanying drawings, wherein like reference numerals denote like elements.

FIG. 4A shows microscopy images illustrating MKs squeezing through 3 µm-wide microchannels, supporting a model of vascular PLT production, in accordance with the present invention.

FIG. 4B shows microscopy images illustrating MKs extending large fragments through 3 µm-wide microchannels, supporting a model of vascular PLT production, in accordance with the present invention.

FIG. 4F is a graphical depiction illustrating that increased shear rates within physiological ranges do not increase proPLT extension rate, in accordance with the present invention.

FIG. 4G shows miscrocopy images illustrating that MKs retrovirally transfected to express GFP-β1 tubulin showed proPLT extensions and were comprised of peripheral MTs that form coils at the PLT-sized ends, in accordance with the present invention.

FIG. 4H is a graphical depiction illustrating that 5 µM Jasplankinolide (Jas, actin stabilizer) and 1 mM erythro-9-(3-[2-hydroxynonyl] (EHNA, cytoplasmic dynein inhibitor) inhibit shear-induced proPLT production, in accordance with the present invention.

FIG. 4I shows microscopy images illustrating drug-induced inhibition of proPLT production under physiological shear, in accordance with the present invention.

FIG. 6G shows microscopy images illustrating that microfluidic device derived-hPLTs are ultrastructurally similar to human blood PLTs and contain a cortical MT coil, open canalicular system, dense tubular system, mitochondria, and characteristic secretory granules in accordance with the present invention. Top-right insert shows peripheral MT coil.

FIG. 6H shows microscopy images illustrating that microfluidic device derived-hPLTs are morphologically similar to human blood PLTs and display comparable MT and actin expression, in accordance with the present invention.

FIG. 6I shows microscopy images illustrating that microfluidic device derived-mPLTs form filpodia/lamellipodia on activation and spread on glass surface, in accordance with the present invention.

DETAILED DESCRIPTION OF THE INVENTION

Figure 1:
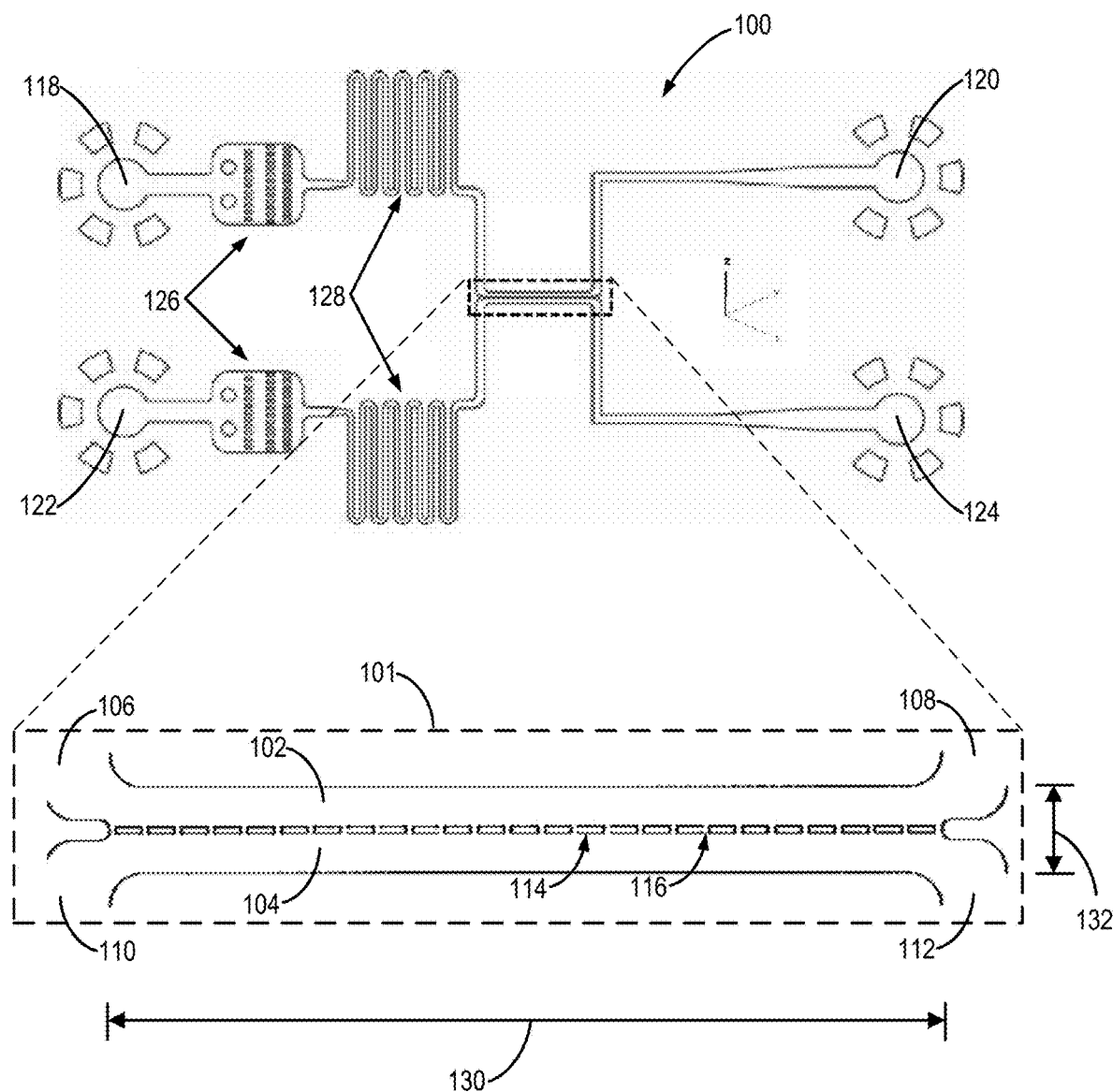
FIG. 1 is a schematic illustration of a biomimetic microfluidic system in accordance with the present invention.

Blood platelets (PLTs) play a critical role in stimulating clot formation and repair of vascular injury. Morbidity and mortality from bleeding due to low PLT count is a major clinical problem encountered across a number of conditions including chemotherapy or radiation treatment, trauma, immune thrombocytopenic purpura (ITP), organ transplant surgery, severe burns, sepsis, and genetic disorders. Despite serious clinical concerns owing to their immunogenicity and associated risks, along with inventory shortages owing to high demand and short shelf life, PLT transfusions total more than 10 million units per year in the United States.

PLT production involves the differentiation of megakaryocyte (MKs), which sit outside sinusoidal blood vessels in the bone marrow (BM) and extend long, branching cellular structures (designated proPLTs) into the circulation. ProPLTs experience vascular shear and function as the assembly lines for PLT production, containing PLT-sized swellings in tandem arrays that are connected by thin cytoplasmic bridges. Although detailed characterization of proPLTs remains incomplete, these structures have been recognized both in vitro and in vivo and proPLT-producing MKs in culture yield PLTs that are structurally and functionally similar to blood PLTs. PLTs are released sequentially from proPLT tips. This mechanism is highly dependent on a complex network of tubulin and actin filaments that function as the molecular struts and girders of the cell. Microtubule (MT) bundles run parallel to proPLT shafts, and proPLT longation is driven by MTs sliding over one another. During proPLT maturation, organelles and secretory granules traffic distally over MT rails to become trapped at proPLT tips. Actin promotes proPLT branching and amplification of PLT ends. Live cell microscopy of murine MKs has been vital to this understanding, however most studies to date have been done in vitro on static MK cultures.

Thrombopoietin (TPO) has been identified as the major regulator of MK differentiation, and it has been used to produce enriched populations of MKs in culture. In one reference, it was demonstrated that human PLTs generated in vitro from proPLT-producing MKs were functional. Since then, MKs have been differentiated from multiple sources, including fetal liver cells (FLCs), cord blood stem cells (CBSCs), embryonic stem cells (ESCs), and induced pluripotent stem cells (iPSCs). However, current 2-D and liquid MK cultures fall orders of magnitude short of the estimated ~2000 PLTs generated per MK in vivo. More recently, modular 3-D knitted polyester scaffolds have been applied under continuous fluid flow to produce up to 6×10$^6$ PLTs/day from 1 million CD34$^+$ human cord blood cells in culture. While suggestive that clinically useful PLT numbers may be attained, those 3-D perfusion bioreactors do not accurately reproduce the complex structure and fluid characteristics of the BM microenvironment, and their closed modular design prevents visualization of proPLT production, offering little insight into the mechanism of PLT release. Alternatively, 3-D polydimethylsiloxane (PDMS) biochips adjacent ECM-coated silk-based tubes have been proposed to reproduce BM sinusoids and study MK differentiation and PLT production in vitro. Although such devices recapitulate MK migration during maturation, they are not amenable to high resolution live-cell microscopy, and fail to reproduce endothelial cell contacts necessary to drive MK differentiation.

While MK differentiation has been studied in culture, the conditions that stimulate proPLT production remain poorly understood, particularly in vivo. MKs are found in BM niches, and some evidence suggests that cell-cell, cell-matrix, and soluble factor interactions of the BM stroma contribute to proPLT formation and PLT release. Indeed, the chemokine SDF-1 and growth factor FGF-4 recruit MKs to sinusoid endothelial cells. Extracellular matrix (ECM) proteins are another major constituent of the BM vascular niche, and evidence suggests that signaling through trans-membrane glycoprotein (GP) receptors regulate proPLT formation, PLT number and size (defects seen in e.g. Bernard-Soulier syndrome, Glanzmann's thrombasthenia). Collagen IV and vitronectin promote proPLT production, which can be inhibited by antibodies directed against their conjugate integrin receptor, GPIbα. Likewise, fibrinogen regulates proPLT formation and PLT release through GPIIbIIIa. While these findings shed light on the environmental determinants of proPLT production, they are limited by a reductionist approach. Therefore, new models that incorporate the defining attributes of BM stroma complexity are necessary to elucidate the physiological regulation of MKs into PLTs.

In the BM, proPLTs experience wall shear rates ranging from, 100 to 10,000 $s^{-1}$ or, more particularly, from 500 to 2500 $s^{-1}$. While the role of continuous blood flow on PLT thrombus formation has been studied, surprisingly little attention has been paid to the mechanism by which shear forces regulate PLT release. When investigated, experiments have not been physiologically representative. Some preliminary studies have perfused MKs over ECM-coated glass slides, which select for immobilized/adhered MKs without discriminating ECM-contact activation from shear. Alternatively, released proPLTs have been centripetally agitated in an incubator shaker, which does not recapitulate circulatory laminar shear flow, does not provide precise control of vascular shear rates, and is not amenable to high-resolution live-cell microscopy. Despite these major limitations, exposure of MKs to high shear rates appears to accelerate proPLT production and while proPLTs cultured in the absence of shear release fewer PLTs than those maintained at fluid shear stresses.

Microfluidic devices provide excellent platforms to generate and precisely tune dynamic fluid flows, and thus mimic blood vessel conditions to deliver chemical cues to cells. Embedding microfluidic networks within cell-laden hydrogels has been shown to support efficient convective transport of soluble factors through 3D scaffolds. Viable 3D tissue contacts have been produced consisting of hepatocytes encapsulated in agarose, calcium alginate hydrogels seeded with primary chondrocytes, and endothelial cells embedded in 3D tubular poly(ethylene glycol) hydrogels. Accordingly, the technology has been applied to the development of organs-on-a-chip, including liver, kidney, intestine, and lung. In addition, recent development of microvasculature-on-a-chip models have been used to study cardiovascular biology and pathophysiology in vitro. These studies emphasize the importance of mimicking the physical microenvironment and natural chemical cues of living organs to study cellular and physiological development. For example, this is particularly important for drug-mediated inhibition of PLT production. Since proPLT-producing MKs sit just outside blood vessels in the BM, interacting with both the semi-solid ECM microenvironment of BM and fluid microenvironment of the circulation, biomimetic microfluidic biochips may achieve a model system to elucidating the relevant physiological mechanisms, such as those responsible for drug-induced thrombocytopenia.

Turning now to FIG. 1, a schematic is shown illustrating an example of a biomimetic system 100 in accordance with various embodiments of the present invention. The system 100 includes a substrate 101, a first channel 102 and a second channel 104, wherein each channel is configured to carry a flow of any fluid medium transporting or consisting of but not limited to, for example, particles, cells, substances, particulates, materials, compositions and the like. In one embodiment, the system 100 and/or substrate 101 may be constructed using cell-inert silicon-based organic polymers, such as polydimethylsiloxane (PDMS).

The first channel 102 includes a first channel input 106 and first channel output 108. Similarly, the second channel 104 includes a second channel input 110 and second channel output 112. The first channel 102 and second channel 104 extend along a substantially longitudinal direction, and are longitudinally and transversally dimensioned, as will be explained, to achieve desired flow profiles, velocities, or rates, such as those present in a physiological system. In one aspect, the size of the longitudinal 130 and transverse 132 dimensions describing the channels may be in a range consistent with an anatomical or physiological structure, assembly, configuration or arrangement, such as in the case of bone marrow and blood vessels. By way of example, the longitudinal 130 dimension may be in the range of 1000 to 30,000 micrometers or, more particularly, in the range of 1000 to 3000 micrometers, and the transverse 132 dimension may be in the range of 100 to 3,000 micrometers or, more particularly, in the range of 100 to 300 micrometers, although other values are possible. In another aspect, each channel may be prepared, conditioned, or manufactured to receive, localize, trap, or accumulate for example, particles, cells, substances, particulates, materials, compositions, and the like, from a traversing fluid medium.

The system 100 also includes a series of columns 114 that separate the first channel 102 and second channel 104. The long axes of the columns 114 are generally arranged parallel to the longitudinal 130 dimension of the channels, the series of columns 114 extending for a distance substantially equal to the longitudinal 130 dimension of the channels. The columns 114 are separated by gaps, creating a series of gaps that, as illustrated, may be microchannels 116 that extend from the first channel 102 to the second channel 104 to create a partial fluid communication path passing between the columns 114. However, the term "microchannel" when referring to the gaps does not connote a particular width. For example, the gaps may be substantially greater or smaller than the micrometer range. In one embodiment, the columns 114 and microchannels 116 are dimensioned such that particles, cells, substances, particulates, materials, compositions, and the like, may bind, adhere to or otherwise be confined to an area generally in the vicinity of the columns 114 and microchannels 116 and, thereby, harvested from an area proximate to the microchannels 116. As an example, the longitudinal 130 and transverse 132 dimensions of the columns 114 may be in the range of 1 to 200 micrometers, while the longitudinal 130 dimension of the microchannels 116, defined by the separation distances or gaps between the columns 114, may be in the range of 0.1 to 20 micrometers, although other values are possible.

Flow in the first channel 102 is established through a first source or input 118 configured for deliver a first medium, and a first outlet 120, configured for extracting the first fluid medium. Similarly, flow of a second fluid medium in the second channel 104 is established through a second source or inlet 122 to a second outlet 124. The first input or source 118 and the second source of inlet 122 may be arranged to include a pump or other system for delivering a controlled flow. In one configuration, the first outlet 120 or second outlet 124 may also be fitted with or followed by elements, components, devices or systems designed to capture, store and/or separate a desired material or substance from a first or second fluid medium, such as for example, human blood platelets, or thrombocytes. That is, flow velocities or flow rates of the first fluid medium between the first channel input 106 and first channel output 108, and of the second fluid medium between the second channel input 110 and second channel output 112, may be established by way of fluid communication of system 100 with any number of sources, such as microfluidic pumps and drains, and may be sustained for any desired or required amount of time. Control and manipulation of flow may be realized by integrating elements, such valves, sources and drains, with the system 100, or may be achieved by external interfacing or coupling of the system 100 with various components for fluid actuation and flow regulation.

As will be described, flow velocities or rates in the first channel 102 may be configured to be substantially different from flow velocities or rates in the second channel 104, as desired, or as required for recapitulating, modeling, or duplicating physiological elements, constituents and conditions such as, for example, those found in bone marrow and blood vessels. In another embodiment, flow velocities or rates may be controlled in a manner that duplicates physiological shear rates and profiles, such as vascular shear rates and profiles.

The system 100 may also include filtration elements 126, which may take any shape or form, arranged along the paths of each of the first and second fluid mediums and designed to capture or remove from the traversing fluid mediums any kind of debris, dust and any other contaminants or undesirable materials, elements, or particulates. In one configuration, filtration elements 126 are situated in proximity to the first inlet 118 and second inlet 122. The system 100 further includes flow resistive elements 128, which may take a variety of shapes or forms, arranged along the paths of each of the first and second fluid mediums and designed to control flow forces or damp fluctuations in flow rate. In one configuration, flow resistive elements 128 may be situated following each of the filtration elements 126 along the paths of each of the first and second fluid mediums.

In one configuration, recreating human bone marrow (BM) vascular niche ex vivo may be achieved by selectively filling the first channel 102 with bone powder, proteins, such as CI, CIV, FG, FN, VN, LN and VWF, gels such as agarose, alginate, and matrigel or solutions such as PBS, HBS, DMEM EGM or other media, alone and in combination. Alternatively, ECM proteins may be patterned directly onto glass surfaces prior to adhesion of biochips to surface slides using protein micro/nano-stamping, or following microfluidic device assembly using parallel microfluidic streams. Local component concentration may be adjusted by regulating microfluidic stream flow rate during infusion, with focus on alignment and 3-D arrangement.

In another configuration, recapitulating human BM vasculature may be achieved by selectively coating the second channel 104 by culturing with endothelial cells at 37 degrees C. and 5 percent $CO_2$. Endothelial cells may be fixed with 4% formaldehyde, and probed for cellular biomarkers to resolve cellular localization and architecture. The second channel 104 of endothelialized BM biochips may be perfused with a fluorescent or colorimetric medium such as FITC-dextran or with beads, and visualized by live-cell microscopy to assess sample/cell/molecule diffusion and determine vascular permeability.

The system 100 in accordance with the present invention can provide a platform for recapitulating physiological conditions, such as those of human BM, by replicating the dimensions, environments and conditions found in human venules using a biomimetic microfluidic device. The microfluidic channels separated by columns spaced closely apart experiencing controlled environments and flow conditions represent a realistic physiological model that may be employed to produce functional PLTs. In this manner, MK trapping, BM stiffness, ECM composition, micro-channel size, hemodynamic vascular shear, and endothelial cell contacts may be tailored to reproduce human BM in vitro.

Specific examples of materials and methods utilized in this approach are detailed below. It will be appreciated that the examples are offered for illustrative purposes only, and are not intended to limit the scope of the present invention in any way. Indeed, various modifications of the invention in addition to those shown and described herein such as the application of this invention to model the blood brain barrier or study molecular diffusion across separate mediums will become apparent to those skilled in the art from the foregoing description and the following examples and fall within the scope of the appended claims. For example, specific dimensions, configurations, materials, cell types, particulates, flow medium and flow rates, fabrication methods and recipes, as well as imaging, processing and analysis methods, and so on, are provided, although it will be appreciated that others may also be used.

EXAMPLES

Microfluidic Device Design and Fabrication

As shown in FIG. 1, microfluidic devices were fabricated using soft lithography, consisting of two channels containing passive filters, for trapping air bubbles and dust, followed by fluid resistors, used to damp fluctuations in flow rate arising during operation. The channels merge to a rectangular area 1300 micrometers long, 130 micrometers wide, and 30 micrometers deep, separated by a series of columns (10 micrometers wide and 90 micrometers long) spaced 3 micrometers apart. To ensure efficient gas exchange and support high-resolution live-cell microscopy during cell culture, microfluidic devices were constructed from a cell-inert silicon-based organic polymer bonded to glass slides.

AutoDesk software in AutoCAD was used to design the desired 2D pattern and printed on a photolithography chrome mask. Silicon wafers (University Wafers, Boston, Mass.) were spin coated with SU-8 3025 photoresist (Michrochem, Newton, Mass.) to a 30 micrometers film thickness (Laurell Technologies, North Wales, Pa.), baked at 65 degrees C. for 1 minute and 95 degrees C. for 5 minutes, and exposed to UV light (~10 mJ $cm^{-2}$) through the chrome mask for 30 seconds. The unbound SU-8 photoresist was removed by submerging the substrate into propylene glycol monomethyl ether acetate for 7 minutes. Polydimethylsiloxane (PDMS) was poured onto the patterned side of the silicon wafer, degassed, and cross-linked at 65 degrees C. for ~12 hours. After curing, the PDMS layer was peeled off the mold and the inlet and outlet holes were punched with a 0.75 mm diameter biopsy punch. The channels were sealed by bonding the PDMS slab to a glass cover slide (#1.5, 0.17× 22×50 mm, Dow Corning, Seneffe, Belgium) following treatment with oxygen plasma (PlasmaPrep 2, GaLa Instrumente GmbH, Bad Schwalbach, Germany). Samples were infused into the microfluidic device via PE/2 tubing (Scientific Commodities, Lake Havasu City, Ariz.) using 1 mL syringes equipped with 27-gauge needles (Beckton Dickinson, Franklin Lakes, N.J.). Flow rates of liquids were controlled by syringe pumps (PHD 2000, Harvard Apparatus, Holliston, Mass.).

Microfluidic Device Operation

Devices were coated with a 0.22 µm filtered 10% BSA solution (Millipore, Billerica, Mass.) for 30 minutes to prevent direct cell contact with glass. Primary MKs and media were infused in the first inlet 118 and second inlet 122, respectively, at a rate of 12.5 µL/hour using a two-syringe microfluidic pump (Harvard Apparatus, Holliston, Mass.). When the first outlet 120 is closed, both input solutions are redirected toward the second outlet 124 causing primary MKs to trap.

Extracellular Matrix Composition Modeling (2D)

Microfluidic devices were selectively coated with extracellular matrix proteins by perfusing the channels with rhodamine-conjugated fibrinogen (1 mg/mL) or fibronectin (50 µg/mL, Cytoskeleon Inc., Denver, Colo.) for 30 minutes. Samples were perfused in parallel through both inlets and collected through both outlets so that laminar flow streams did not mix. Devices were washed with 1× PBS and coated with 0.22 µm filtered (Millipore, Billerica, Mass.) 10% BSA solution (Roche, South San Francisco, Calif.) for 30 minutes to coat any remaining exposed glass.

BM Stiffness Modeling (3D)

Primary MKs were re-suspended in 1% sterile alginate with an average molecular weight of 150-250 kD (Pronova SLG100, FMC biopolymer, Norway) in culture media and perfused across the microfluidic device (first inlet 118, second outlet 124) until MKs became trapped. The second channel was then selectively perfused with 1×PBS to remove alginate from this channel. To make a homogenous alginate gel, 30 mM nanoparticle calcium carbonate (mkNANO, Canada) was used as a calcium source and dissolved in 60 mM slowly hydrolyzing D-Glucono-δ-lactone (Sigma-Aldrich, St. Louis, Mo.), which releases the calcium in the solution (in review Khavari et al NJP 2013). The calcium carbonate suspension was perfused along the second channel until the alginate solution retained in the first channel became polymerized (~20 minutes). The second channel was then selectively washed with 1× PBS and replaced with culture media. To determine the alginate gel's mechanical properties 0.25 percent, 0.5 percent, 1.0 percent, and 2.0 percent alginate gels were prepared and their frequency-dependent shear moduli were measured by rheology at 37° C. (Ares G2 TA instruments, New Castle, Del.).

Sinusoidal Blood Vessel Contact Modeling (3D)

Microfluidic devices were selectively coated with 50 µg/mL fibronectin (Cytoskeleon Inc., Denver Colo.) and 10 percent BSA (Roche, South San Francisco, Calif.), as described above, and transferred to a 37 degrees C., 5 percent CO2 incubator. 10,000,000 HUVECs/mL in EBM media (Lonza, Basel, Switzerland) were seeded over the fibronectin-coated channel at 12.5 uL/hour and permitted to adhere to this surface over a period of 3 hours. The inlet sample was replaced with cell-free EBM media and perfused through the channel until HUVECs reached confluency (2-8 days). Cells were stained with 5 µM CellTracker Red and 1 µg/mL Hoescht 33342 (Invitrogen, Carlsbad, Calif.) for 45 minutes, washed in fresh media or fixed in 4% formaldehyde and visualized by confocal-fluorescence microscopy.

Vascular Shear Rate Modeling (3D)

The shear stresses imparted on the MKs were estimated with a computational model of the fluid dynamics within the microfluidic device. A commercial finite element method software (COMSOL) was used to solve the Navier-Stokes equation. The steady-state Navier Stokes flow equation for incompressible flow is:

$$\rho(\vec{v} \cdot \vec{\nabla} \vec{v}) = -\vec{\nabla}_{=p} + \mu \vec{\nabla}^2 \vec{v} + f \qquad (1)$$

where $\rho$ is the fluid density, $\vec{v}$ is the flow velocity, $p$ is the pressure, $\mu$ is the fluid viscosity and f is the body forces action on a fluid. Equation (1) was solved in a three dimensional computational domain replicating the exact dimensions of the microfluidic device. It was assumed that the fluid within the device had a viscosity and density of water (0.001 Pa s and 1000 kg/m3, respectively). No slip boundary conditions were assumed at the walls of the channels. The infusion flow rates ranged from 12.5-200 µL/hr. A triangular mesh, which was made finer at the slits, was used to discretize the domain. The model contained 315,317 degrees of freedom. Mesh independence, as was confirmed by obtaining less than a 10 percent difference between shear rates, was found between 251,101 and 415,309 degrees of freedom. The steady state solutions were obtained using the UMFPACK linear system solver.

Primary Mouse Megakaryocyte Culture

Mouse FLCs were collected from WT CD1 mice (Charles River Laboratories, Wilmington, Mass.) and MKs were cultured.

Electron Microscopy

Megakaryocyte input and bioreactor effluent were fixed with 1.25 percent paraformaldehyde, 0.03 percent picric acid, 2.5 percent glutaraldehyde in 0.1-M cacodylate buffer (pH 7.4) for 1 h, post-fixed with 1% osmium tetroxide, dehydrated through a series of alcohols, infiltrated with propylene oxide, and embedded in epoxy resin. Ultrathin sections were stained and examined with a Tecnai G2 Spirit BioTwin electron microscope (Hillsboro, Oreg.) at an accelerating voltage of 80 kV. Images were recorded with an Advanced Microscopy Techniques (AMT) 2-K charged coupled device camera, using AMT digital acquisition and analysis software (Advanced Microscopy Techniques, Danvers, Mass.).

Immunofluorescence Microscopy

Megakaryocytes, released proPLTs, or bioreactor effluent were purified and probed. Samples were either incubated with 5 µM CellTracker Green (Invitrogen, Carlsbad, Calif.) for 45 minutes, washed in fresh media and visualized by live-cell fluorescence microscopy, or fixed in 4% formaldehyde and centrifuged onto poly-L-lysine (1 µg/mL)-coated coverslides. For analysis of cytoskeletal components, samples were permeabilized with 0.5 percent Triton-X-100, and blocked in immunofluorescence blocking buffer (0.5 g BSA, 0.25 ml 10% sodium azide, 5 ml FCS, in 50 ml 1×PBS) overnight before antibody labeling (55). To delineate the microtubule cytoskeleton, samples were incubated with a rabbit polyclonal primary antibody for mouse or human β1-tubulin. To delineate the actin cytoskeleton, samples were incubated with Alexa 568 phalloidin (Invitrogen, Carlsbad, Calif.). Cell nuclei were labeled with 1 μg/mL Hoescht 33342 (Invitrogen, Carlsbad, Calif.). To correct for background fluorescence and nonspecific antibody labeling, slides were incubated with the secondary antibody alone, and all images were adjusted accordingly. Samples were examined with a Zeiss Axiovert 200 (Carl Zeiss, Thornwood, N.Y.) equipped with 10× (numerical aperature, 0.30) Plan-Neofluar air and 63× (numerical aperature, 1.4) Plan-ApoChromat oil immersion objectives, and images were obtained using a CCD camera (Hamamatsu Photonics, Boston, Mass.). Images were analysed using the Metamorph version 7.7.2.0 image analysis software (Molecular Devices, Sunnyvale, Calif., USA) and ImageJ version 1.47p software (NIH, http://rsb.info.nih.gov.ezp-prod1.hul.harvard.edu/ij/).

Cell Size and Morphology Determination

Cells were individually thresholded and high-content cytoplasmic area and perimeter measurements were performed in ImageJ using investigator-coded software, outlined below. Analysis was confirmed by manual inspection of all samples, and improperly thresholded cells were excluded from the analysis. MK diameters were calculated from area measurements to account for non-circular cells. More than 2000 cells were counted for each condition, and analysis of MK area and effluent composition was performed for at least three independent samples. Statistical significance was established using a 2-tailed Student t test for paired samples. Error bars represent one standard deviation about the mean.

Live Cell Microscopy

For shear cultures, MKs were loaded onto 'naked' microfluidic devices (only BSA-coated), and the infusion rate was doubled incrementally from 12.5 μL/hr to 200 μL/hr over a 2 hour period. For static cultures, isolated MKs were pipetted into chambers formed by mounting a glass coverslide coated with 3% BSA onto a 10 mm petri dish with a 1 cm hole and cultured for 24 hours. Both static and shear cultures were maintained at 37 degrees C. and 5 percent CO2 and examined on a Zeiss Axiovert 200 (Carl Zeiss, Thornwood, N.Y.) equipped with 10× (numerical aperature, 0.30) Plan-Neofluar air objective. Differential interference contrast (DIC) images were obtained using CCD camera (Hamamatsu Photonics, Boston, Mass.) at either 2 second (shear cultures) or 20 minute (static cultures) intervals. Images were analyzed using the Metamorph version 7.7.2.0 image analysis software (Molecular Devices, Sunnyvale, Calif., USA) and ImageJ software version 1.47p. ProPLT extension rates were determined manually for over 200 MKs from at least three independent samples. For PLT spreading experiments, effluent was collected from microfluidic devices after 2 hours and pipetted into uncoated static culture chambers, described above. PLTs were permitted to contact glass by gravity sedimentation and spreading was captured at 5 second intervals over a 5 minute period.

GFP-β1 Tubulin Retro Viral Transfection

Dendra2-fused β1 tubulin was cloned into pMSCV plasmids. HEK 293 cells packaging cells were cultured in DMEM supplemented with 10% fetal bovine serum (FBS) to 30-50 percent confluency. Transfection of HEK 293 cells was performed using 2 μg of DNA plasmids encoding gag/pol, vsvG, and the β1 tubulin fused with Dendra2 in the pMSCV vector. After medium exchange the following day, cells were incubated for 72 hours for virus production. The supernatant was filtered through a 0.22 μm filter (Millipore, Billerica, Mass.), and aliquots were stored at −80 degrees C. On the second day of culture, MKs isolated from fetal liver cultures described above were resuspended in DMEM containing 10 percent FBS, 8 μg/mL polybrene (Sigma), and the retroviral supernatant. Samples were transferred to a 6-well plate, centrifuged at 800×g for 90 minutes at 25 degrees C. and then incubated at 37 degrees C. for 90 minutes. Following incubation, MKs were washed by centrifugation and resuspended in fresh DMEM containing 10 percent FBS and TPO. MKs were allowed to mature until day 4 of culture and then isolated by a BSA gradient, as previously described.

Flow Cytometry

Platelets were collected from the released proPLT fraction of static MK cultures or bioreactor effluent and examined under resting conditions. Samples were probed with FITC-conjugated antibodies against CD42a or CD41/61 (Emfret Analytics, Eibelstadt, Germany) and run on a FACSCalibur flow cytometer (Beckton Dickinson). PLTs were gated by their characteristic forward- and side-scattering as they passed through the detector, and their total fluorescence intensity was calculated after subtraction of a FITC-conjugated IgG antibody specificity control (Emfret Analytics). Quantization of PLT yield was determined by dividing net GP IX+ PLT production by net GP IX+ MK depletion over effluent collection period, and was performed for at least 3 independent samples Results were identical for GP IIbIIIa+ cells.

Image Analysis

The digital images acquired in Metamorph were analyzed using ImageJ and Adobe Photoshop CS3 (Adobe Systems, San Jose, Calif.). Dividing lines explicitly separate different images, or separate regions of the same image. No specific features within an image were enhanced, obscured, moved, removed, or introduced, and adjustments made to the brightness, contrast, and color balance were linearly applied to the whole image.

Microfluidic Device Models Physiological Characteristics of Human BM

Figure 2A:
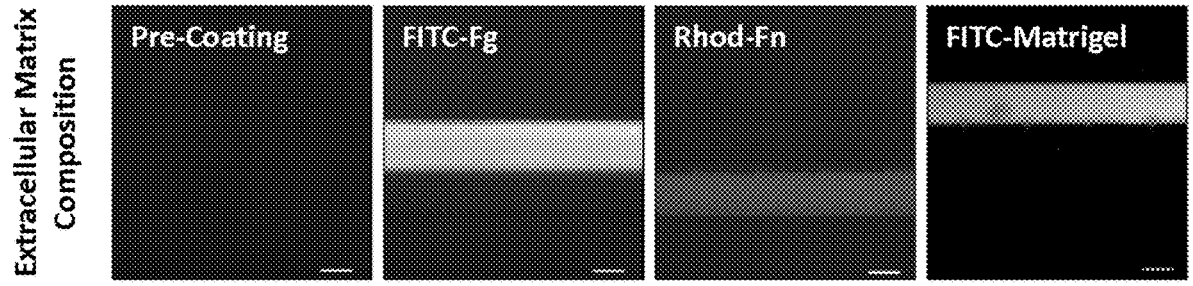
FIG. 2A shows microscopy images depicting a coating of each microfluidic channel with bone marrow and blood vessel proteins to reproduce extra-cellular matrix (ECM) composition, in accordance with the present invention.
Figure 2B:
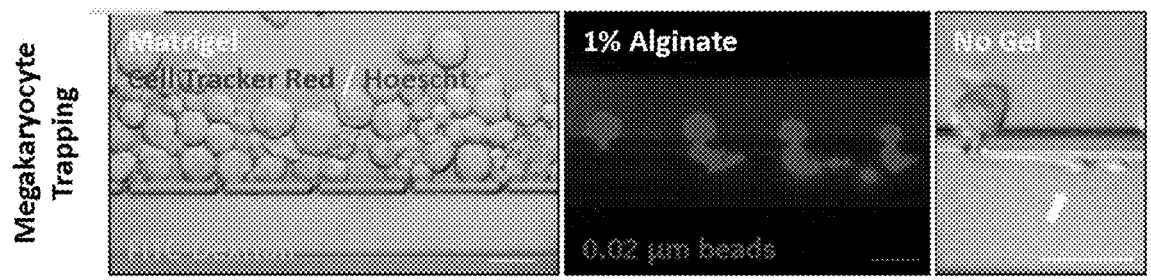
FIG. 2B shows microscopy images depicting megakaryocytes (MKs) trapped in gaps or microchannels selectively embedded in alginate gel (white arrow), modeling 3-dimensional ECM organization and physiological bone marrow (BM) stiffness, in accordance with the present invention.

To recapitulate physiological conditions, each of the channels were selectively coated with fibrinogen and fibronectin, respectively to reproduce ECM composition of the BM and blood vessel microenvironments (shown in FIG. 2A). By running flow across the microfluidic device, primary MKs infused along a first channel would become sequentially trapped between the columns and extend proPLTs into the second channel (shown in FIG. 2B), recapitulating physiological proPLT extension. To model 3D ECM organization and physiological BM stiffness (250 Pa), MKs were infused in a 1 percent alginate solution that was polymerized within the microfluidic device, selectively embedding the MKs in alginate gel within the first channel while retaining vascular flow in the second channel. Alginate did not inhibit proPLT production, and MK distance from the second channel could be controlled.

Figure 2C:
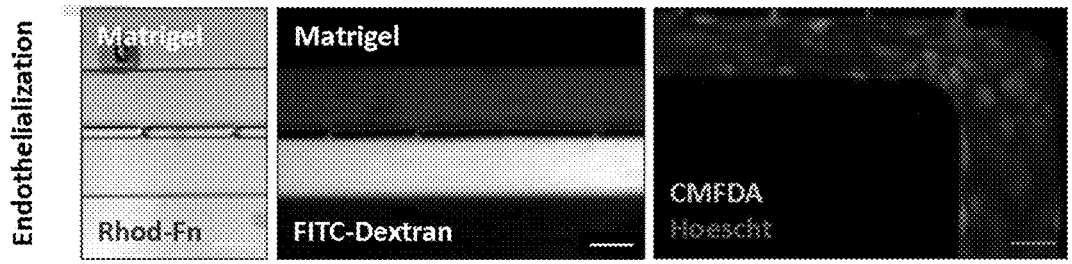
FIG. 2C shows microscopy images of human umbilical vein endothelial cells (HUVECs) selectively cultured in the fibrinogen-coated second channel to produce a functional blood vessel, in accordance to the present invention.
Figure 2D:
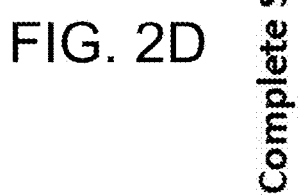
FIG. 2D shows a combined image of the complete system.
Figure 2E:
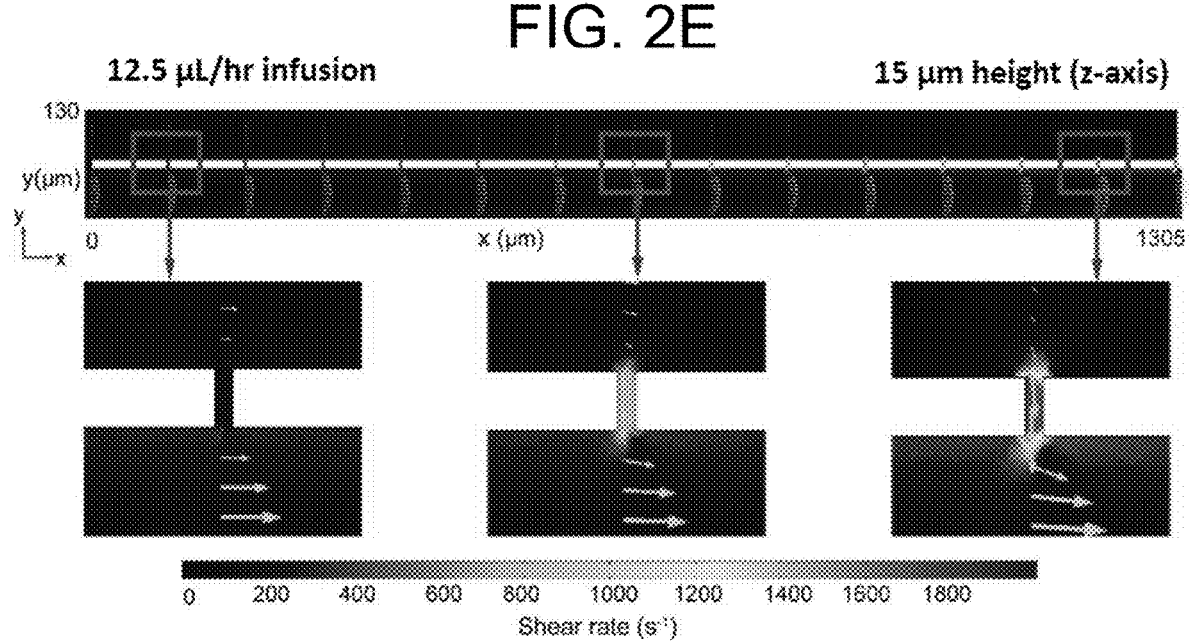
FIG. 2E is a graphical depiction of a simulated distribution of shear rates within a biomimetic microfluidic system in accordance with the present invention.
Figure 2F:
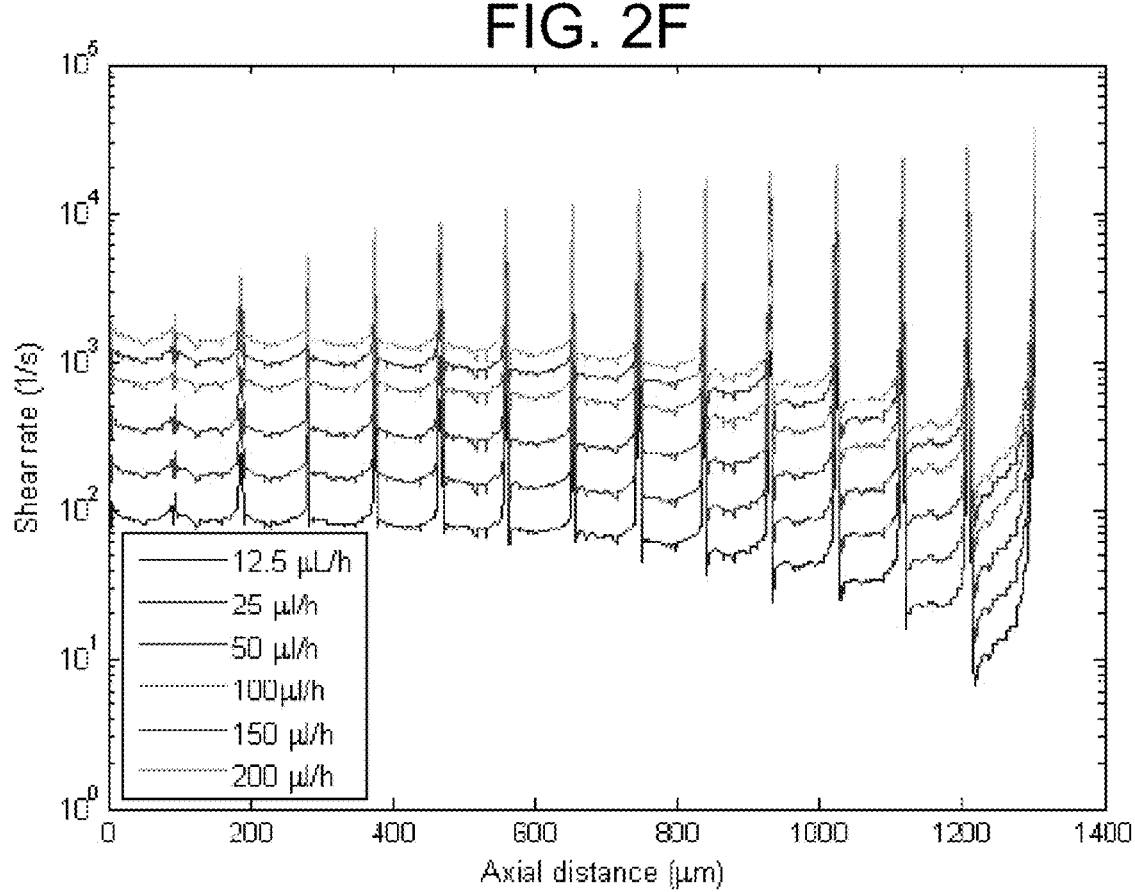
FIG. 2F is a graphical depiction of shear rates as a function of transverse (axial) distance from first channel for several infusion rates, in accordance with the present invention.
Figure 2G:
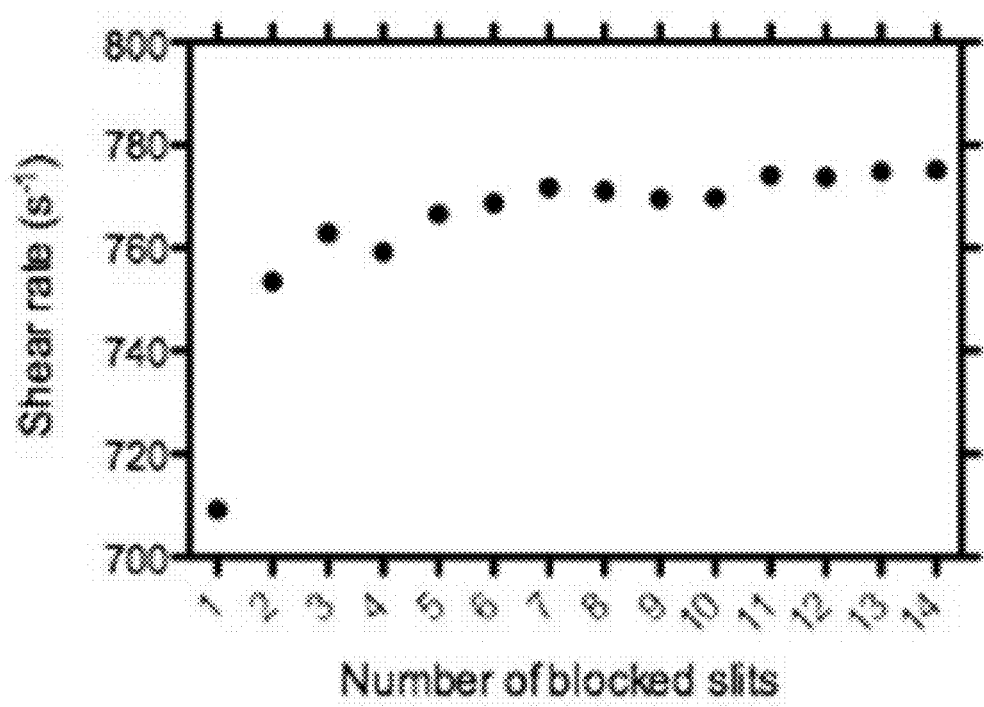
FIG. 2G is a graphical depiction of shear rates as a function of the number of block microchannels (slits or pores), in accordance with the present invention.

Human umbilical vein endothelial cells (HUVECs) were selectively seeded along the second channel, and grown to confluency to produce a functional blood vessel (shown in FIG. 2C). In addition, MK behavior was monitored by 10×-150× magnification, high-resolution live-cell microscopy, and the released PLTs were collected from the effluent. FIG. 2D shows the complete system illustrating operation. Laminar fluid shear rates were characterized (shown in FIG. 2E), and were tightly controlled using two microfluidic pumps (one for the first channel and one for the second channel). Shear rates within the device were linearly proportional to infusion rates and were adjusted to span the physiological range (500-2500 $s^{-1}$). While shear rates at empty microchannel junctions increased with distance from the first channel (shown in FIG. 2F), upon a MK trapping, flow was redirected to the next available gap such that MKs continued to experience physiological (between 760 and 780 $s^{-1}$) shear rates at these sites (shown in FIG. 2G).

Vascular Shear Triggers proPLT Production, Physiological Extension, and Release

Figure 3A:
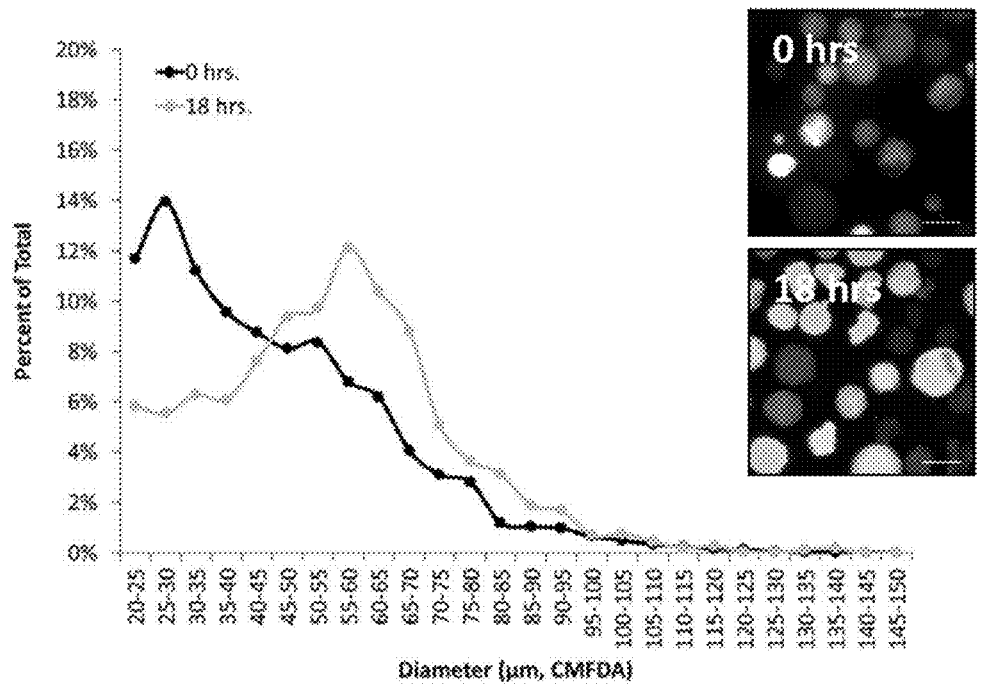
FIG. 3A is a graphical of depiction the diameter distribution for cultured MKs at 0 and 18 hours, in accordance with the present invention.

In vivo BM MKs extend proPLTs in the direction of blood flow and release PLTs, proPLTs, large cytoplasmic fragments (prePLTs), and even whole MKs into sinusoidal blood vessels which may be trapping in the pulmonary microvascular bed, or otherwise maturing in the circulation. To determine the effect of physiological shear on PLT production, mouse fetal liver culture-derived (mFLC) MKs were isolated on culture day 4 and characterized by size and ploidy before being infused into the microfluidic device (shown in FIG. 3A).

Figure 3B:
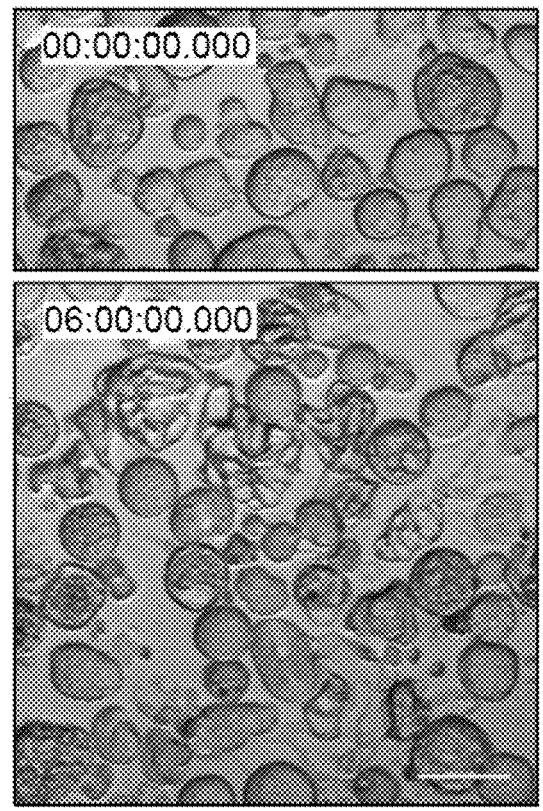
FIG. 3B shows microscopy images of MKs in static culture illustrating the production of proPLTs at 6 hours post-purification, in accordance with the present invention.
Figure 3C:
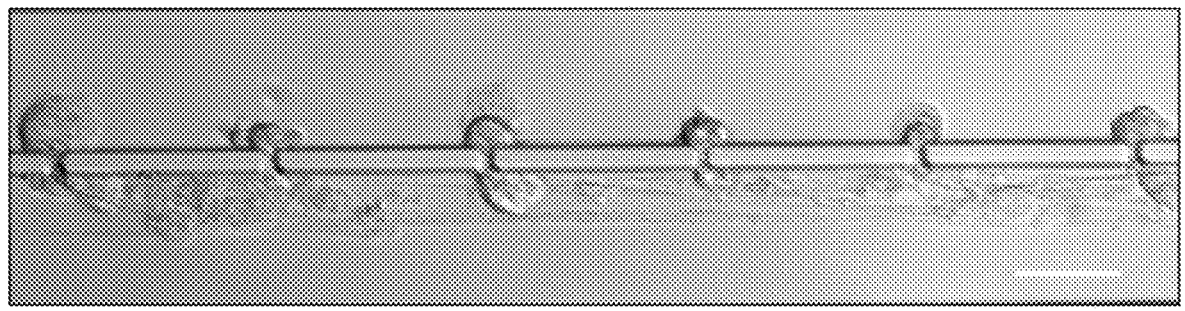
FIG. 3C shows microscopy images of MKs under physiological shear illustrating the production proPLTs immediately upon trapping, in accordance with the present invention.
Figure 3D:
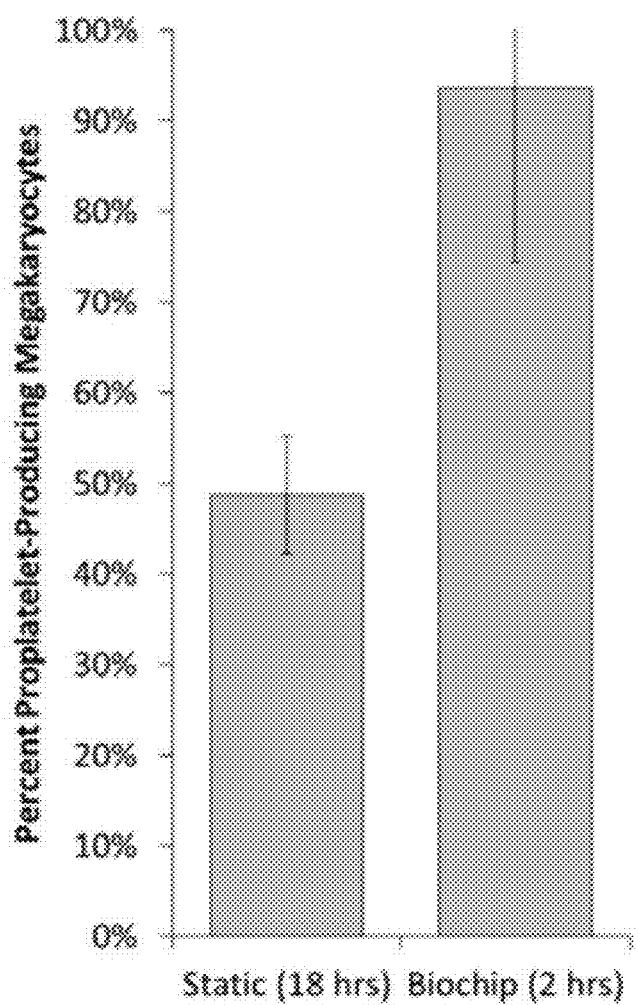
FIG. 3D is a graphical depiction of an increased percentage of proPLT-producing MKs under physiological shear over those of static cultures, in accordance with the present invention.

One of the major challenges in producing transfuseable PLTs in vitro has been identifying factors that trigger proPLT production. Under static conditions MKs begin producing proPLTs ~6 hours post-isolation, and reach maximal proPLT production at 18 hours (shown in FIG. 3B). By comparison, MKs under physiological shear (shown in FIG. 3C at roughly 500 $s^{-1}$) began producing proPLTs within seconds of trapping, reaching maximal proPLT production and biochip saturation within the first 2 hours of culture. MKs cultured under physiological shear produced fewer, longer proPLTs that were less highly branched relative to static cultures. ProPLTs in shear cultures were uniformly extended into the lower channel and aligned in the direction of flow against the vascular channel wall, recapitulating physiological proPLT production. The percent of proPLT-producing MKs under physiological shear were doubled over static cultures to roughly 90% (shown in FIG. 3D).

Figure 3E:
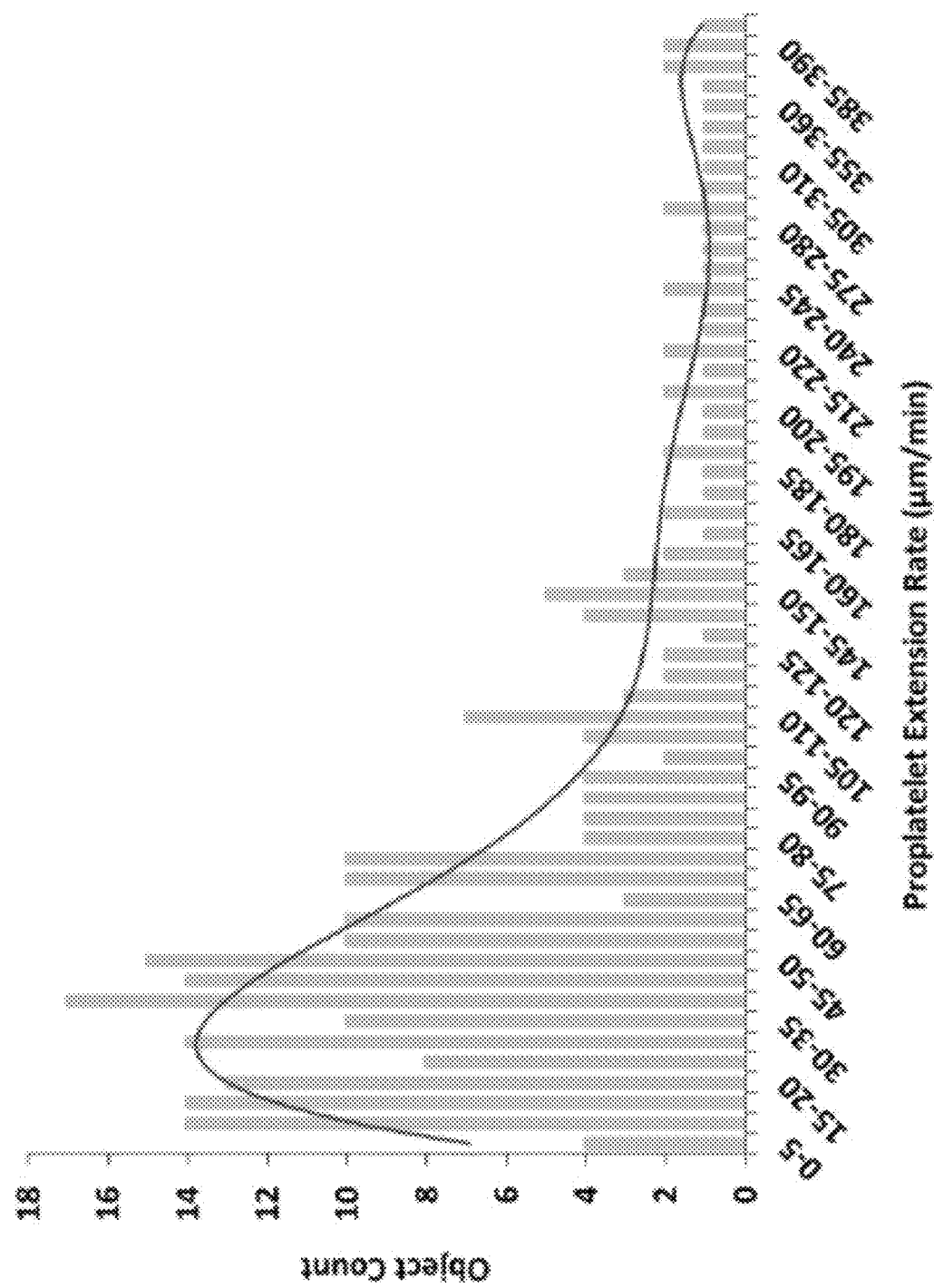
FIG. 3E is a graphical depiction illustration that proPLT extension rates under physiological shear are increased significantly as compared to static cultures, in accordance with the present invention.

Another major challenge in generating clinical numbers of PLTs for infusion has been that in vitro cultures extend proPLTs at a significantly slower rate than what has been observed in vivo. Application of physiological shear in our microfluidic device increased proPLT extension rate by an order of magnitude above static culture controls to roughly 30 μm/min (shown in FIG. 3E), which agrees with physiological estimates of proPLT extension rate from intravital microscopy studies in living mice and support increased PLT production in vitro.

Early histological studies in both humans and mice have predicted that whole MKs, as well as MK fragments may be squeezing through gaps or fenestrations in the vascular endothelium lining BM blood vessels to trap in the pulmonary circulatory bed. Large PLT intermediates called prePLTs were recently discovered in blood, and venous infusion of mBM- and FLC-derived MKs and prePLTs into mice produced PLTs in vivo. In the present study, 100 μm+ diameter MKs were routinely observed squeezing through 3 μm (shown in FIG. 4A) and 1.5 μm gaps, or extending large MK fragments (shown in FIG. 4B), supporting a model of vascular PLT production. In addition, abscission events were routinely captured by high-resolution live-cell microscopy and occurred at variable positions along the proPLT shaft, releasing both prePLT-sized intermediates (3-10 μm diameter) and PLTs (1.5-3 μm diameter) (shown in FIG. 4C and FIG. 4D). Following each abscission, the resulting proPLT end formed a new PLT-sized swelling at the tip, which was subsequently extended and released, repeating the cycle (shown in FIG. 4E).

Figure 4C:
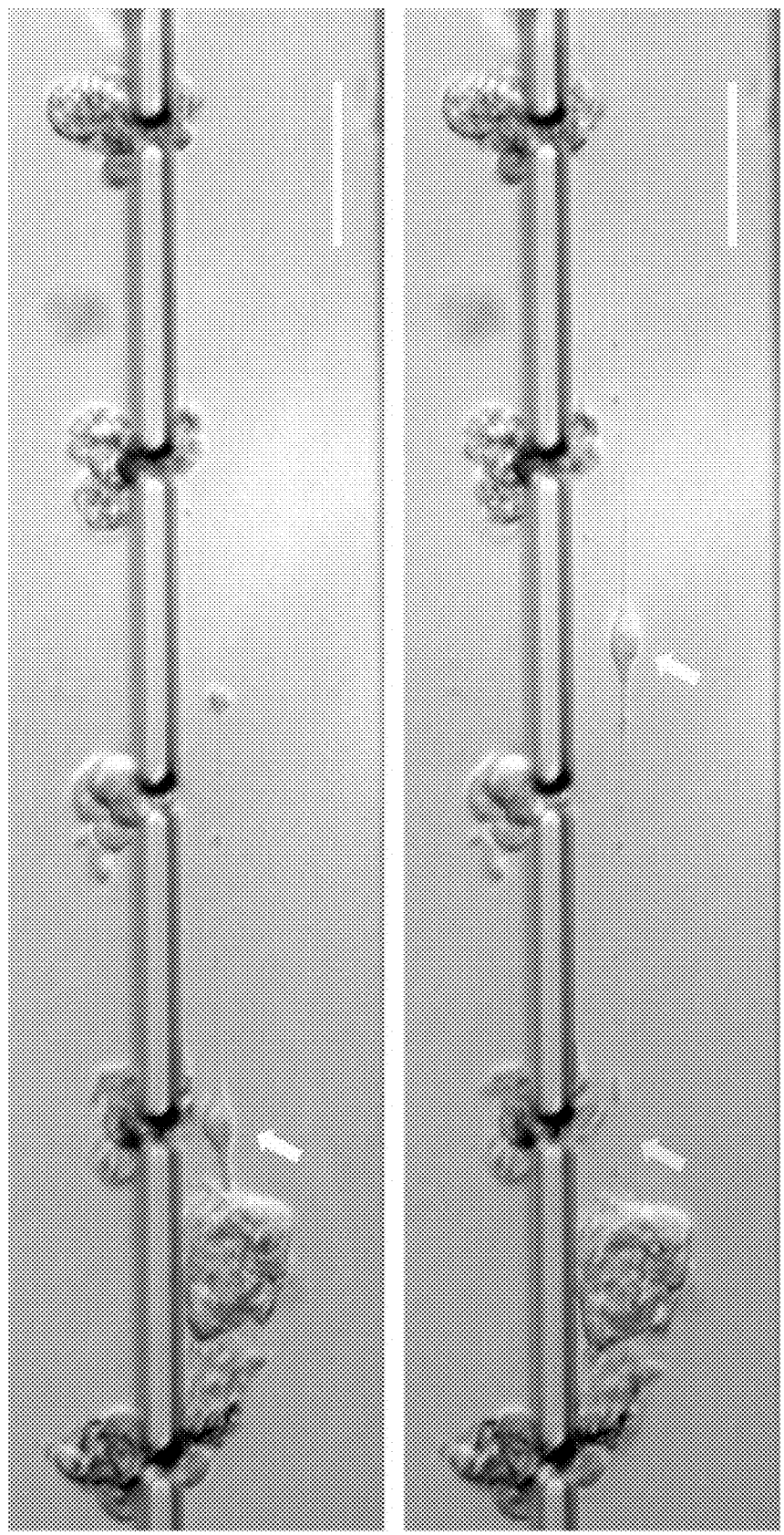
FIG. 4C shows microscopy images illustrating proPLT extension, in accordance with the present invention.
Figure 4D:
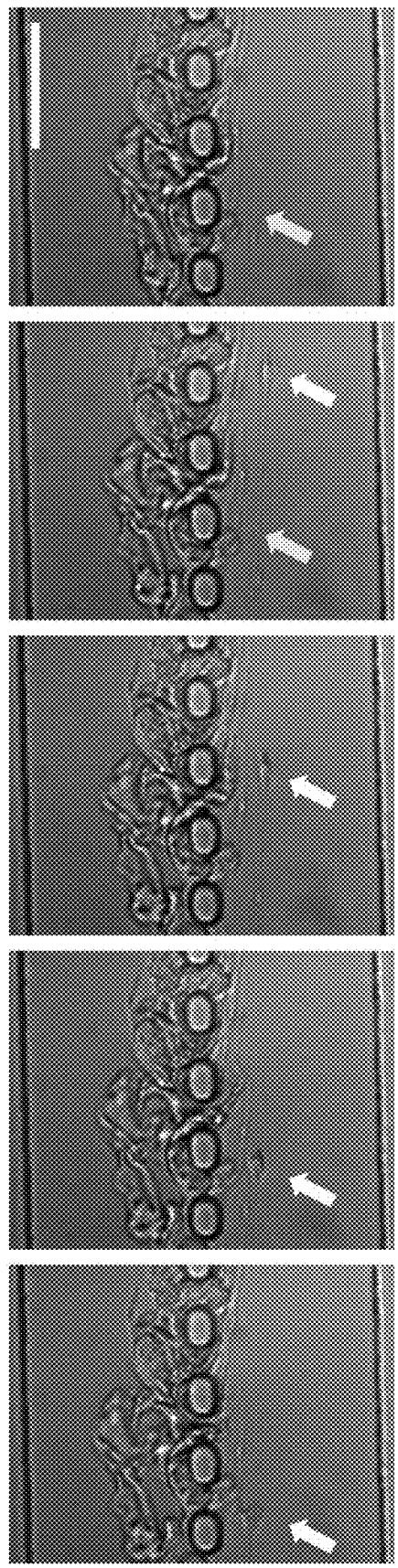
FIG. 4D shows microscopy images illustrating proPLT extension and abscission events at different positions along the proPLT shaft, in accordance with the present invention.
Figure 4E:
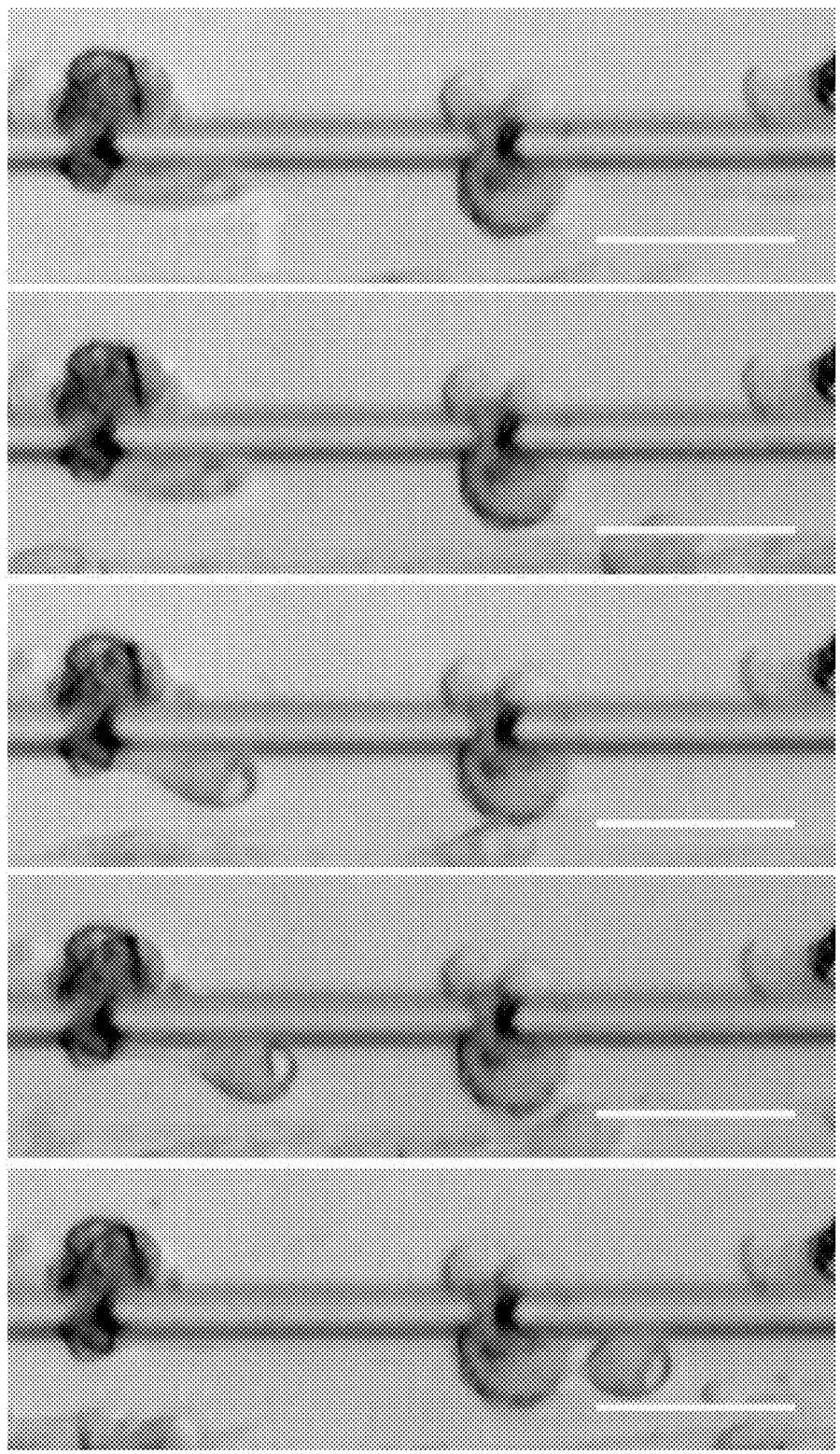
FIG. 4E shows microscopy images illustrating that following abscission, the resulting proPLT end formed a new PLT-size swelling at the tip, which was subsequently extended and released, with the cycle repeated, in accordance with the present invention.

While shear rates were kept constant, proPLT extension rates varied at different positions along the shaft, predictive of a regulated cytoskeletal driven mechanism of proPLT elongation (shown in FIG. 4C). Increasing microfluidic shear rates within the physiological range did not affect the median proPLT extension rate or the distribution of proPLT extension rates in culture (shown in FIG. 4F), and proPLT projections in MKs retrovirally transfected to express GFP-β1 were comprised of peripheral microtubules (MTs) that formed coils at the PLT-sized ends (shown in FIG. 4G). ProPLTs reached lengths exceeding 5 mm, and resisted shear rates up to 1000 $s^{-1}$ in vitro; recapitulating physiological examples of proPLT production from intravital microscopy, and demonstrating that abcission events were not caused by shear. To confirm that shear-induced proPLT extension was cytoskeletal-driven, MKs were incubated with 5 μM Jasplankinolide (Jas, actin stabilizer) or 1 mM erythro-9-(3-[2-hydroxynonyl] (EHNA, cytoplasmic dynein inhibitor) prior to infusion in microfluidic device. Both Jas and EHNA inhibited shear-induced proPLT production (shown in FIG. 4H and FIG. 4I) and PLT release under both static and physiological shear conditions.

Derived PLTs Manifest Structural and Functional Properties of Blood PLTs

Figure 5A:
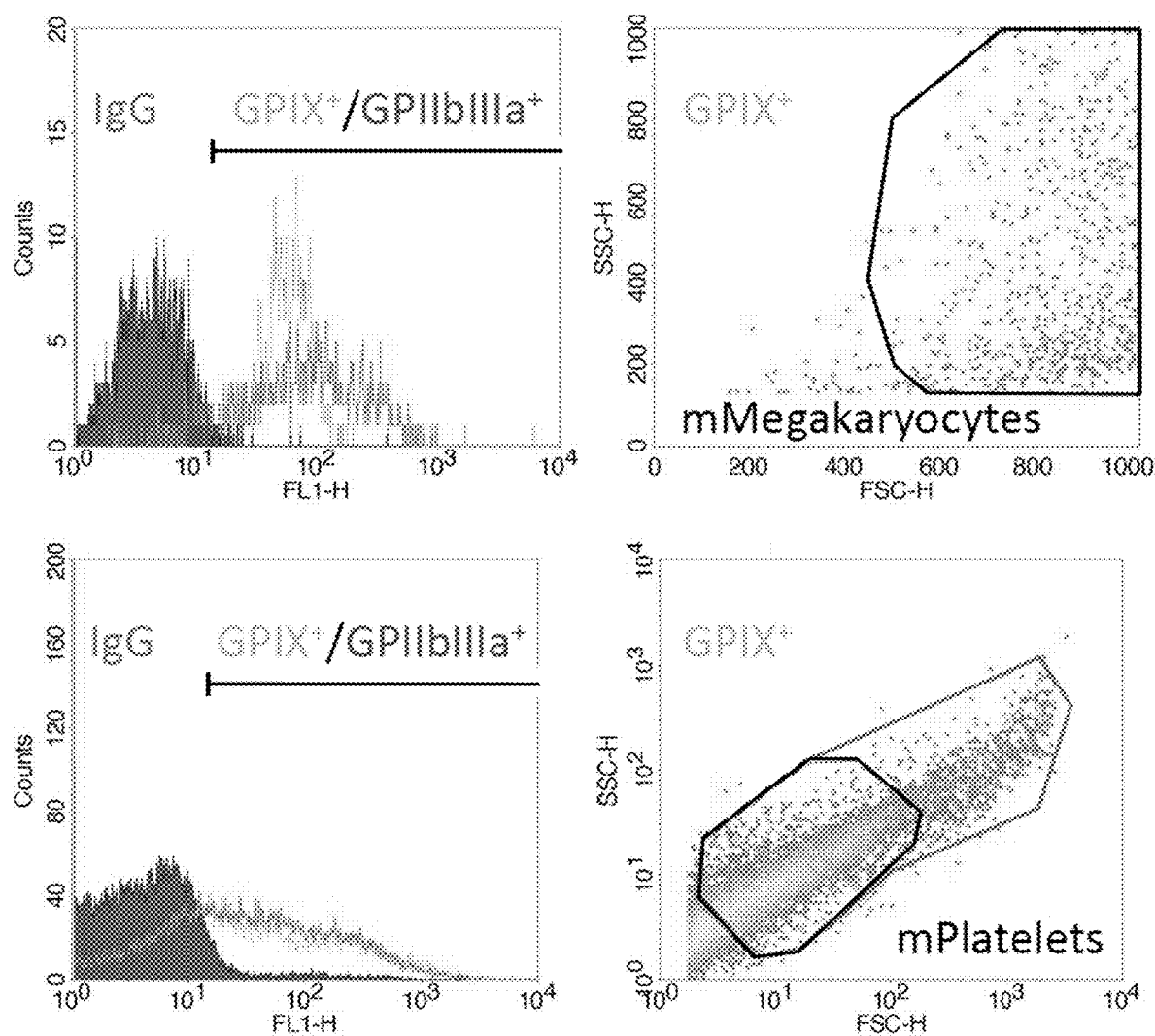
FIG. 5A is a graphical depiction illustrating that microfluidic device-derived mFLC-PLTs manifest structural and functional properties of blood PLTs, in accordance with the present invention.
Figures 5B, 5C:
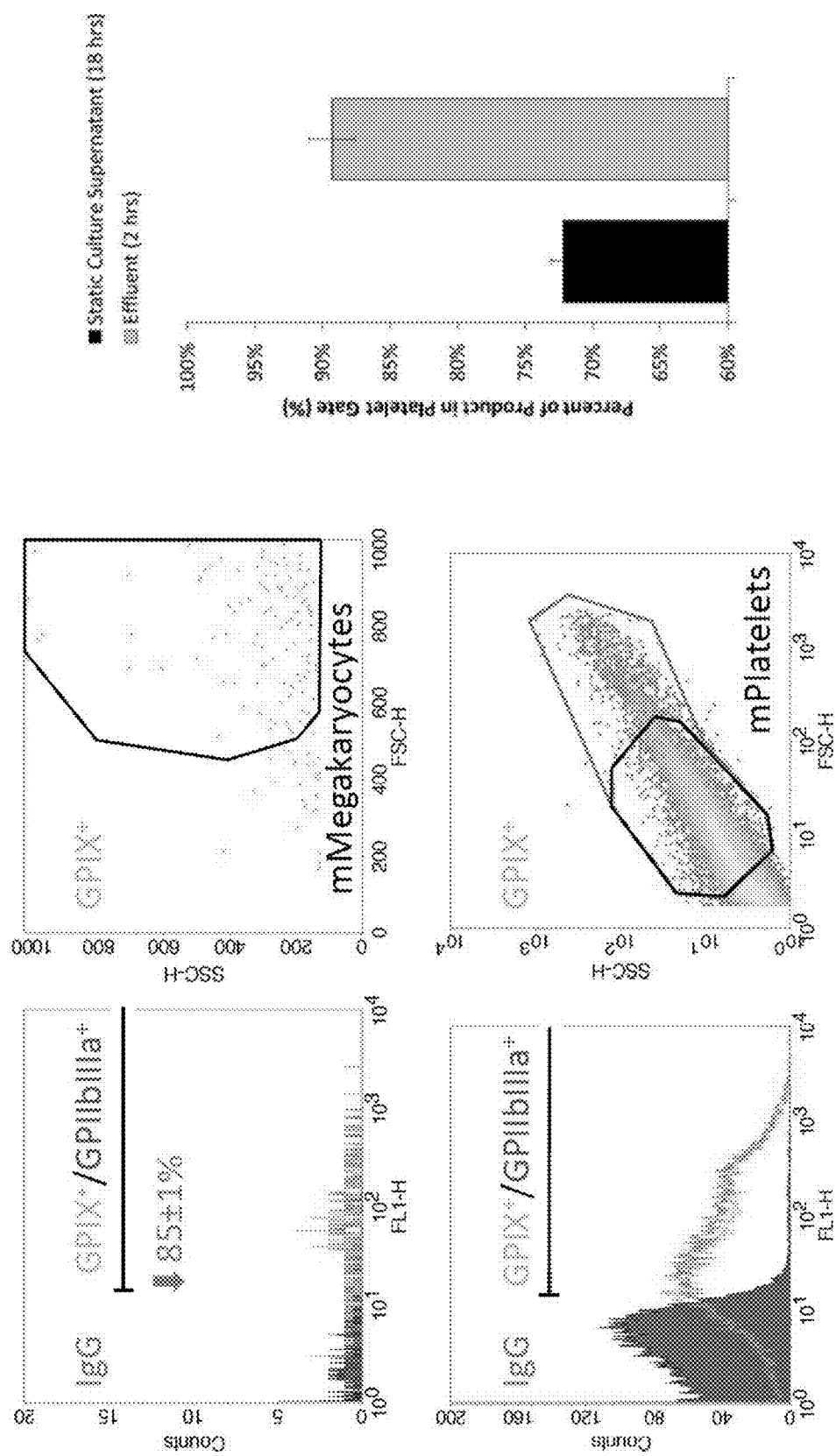
FIG. 5B is a graphical depiction illustrating biomarker expression, and forward/side scatter and relative concentration of GPIX+ mFLC-MKs infused into the microfluidic device following isolation on culture day 4, and effluent collected from the microfluidic device 2 hours post infusion, in accordance with the present invention.
FIG. 5C is a graphical depiction illustrating that the application of shear shifts GPIX+ produce toward more PLT-sized cells relative to static culture supernatant, in accordance with the present invention.
Figure 5E:
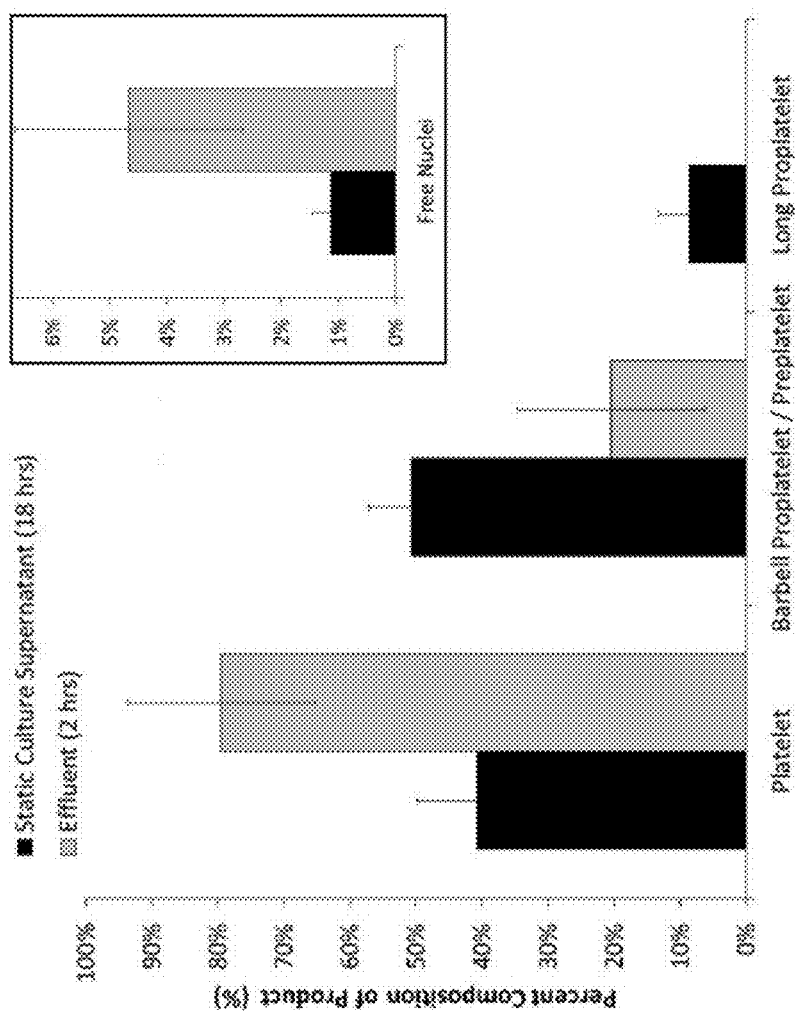
FIG. 5E is a graphical depiction illustrating that the application of shear shifts product toward more PLT-sized β1 tubulin+ Hoescht– cells relative to static culture supernatant, in accordance with the present invention. The insert shows quantitation of free nuclei in the effluent.
Figure 5D:
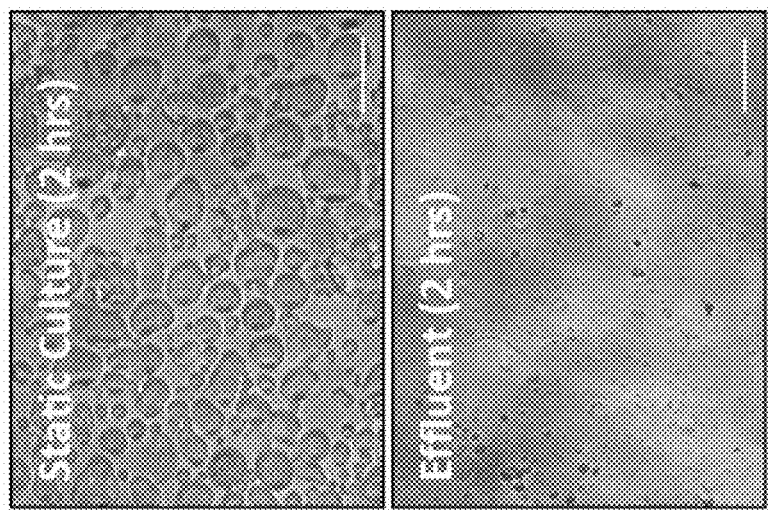
FIG. 5D shows microscopy images illustrating that in the microfluidic device, mFLC-MKs are converted into PLTs over a period of 2 hours, in accordance with the present invention.

PLTs are anucleate discoid cells ~1-3 μm in diameter that express biomarkers GP IX and IIbIIIa on their surface, and are characterized by a cortical MT coil of 6-8 MTs encircling an actin-based cytoskeletal network. To establish PLT yield, biomarker expression, and forward/side scatter and relative concentration of glycoprotein (GP) IX+ mFLC-MKs were measured by flow cytometry immediately before infusion in our microfluidic device on culture day 4 (shown in FIG. 5A). Effluent was collected 2 hours post infusion and compared to mFLC-MK input (shown in FIG. 5B). Input MKs and effluent PLTs both expressed GP IX and IIbIIIa on their surface, and displayed characteristic forward/side scatter. The application of shear shifted the cellular composition of the effluent toward more PLT-sized GPIX+ cells relative to static culture supernatant isolated on culture day 5 (shown in FIG. 5C). 85±1% of MKs were converted into PLTs over 2 hours, which agreed with our quantitation of percent proPLT production (FIG. 3D) and constitutes a significant improvement over static cultures (FIG. 5D). Continuous perfusion of roughly 500 $s^{-1}$ shear over 2 hours in our microfluidic device yielded roughly 21 PLTs per MK and constitutes a major advance in PLT production rate over existing culture approaches that generate comparable PLT numbers over a much longer period of time (6-8 days).

To quantify the morphological composition of our product, the effluent from our microfluidic device was probed for β1 tubulin (PLT-specific tubulin isoform) and Hoescht (nuclear dye), and analyzed by immunofluorescence microscopy. Cells were binned according to their morphology and size, and compared to static MK culture supernatants. The application of shear shifted the cellular composition of the effluent toward more PLT-sized β1 tubulin+ Hoescht− cells (shown in FIG. 5E), which agreed with flow cytometry data (FIG. 5C) and resulted in a product that was more similar in composition to the distribution of PLT intermediates in whole blood. Quantitation of free nuclei in effluent confirmed increased microfluidic device-mediated PLT production relative to static cultures and established PLT yields of roughly 20±12 PLTs per MK, which agree with flow cytometry data.

Figure 5F:
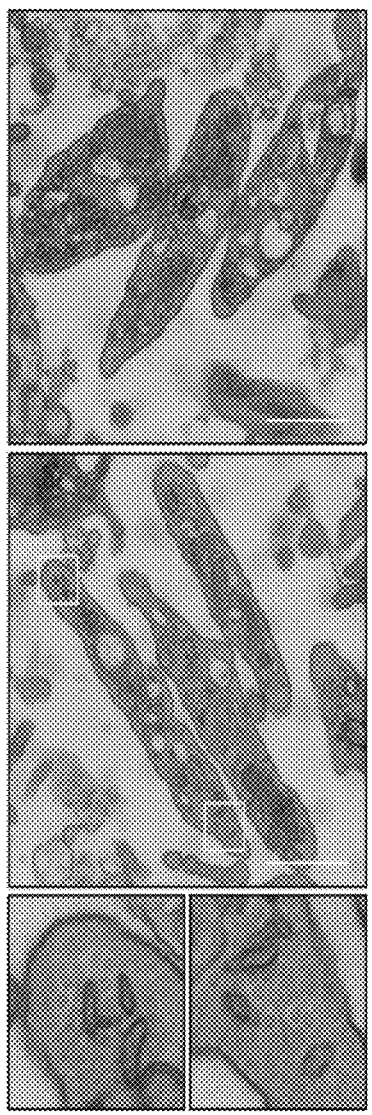
FIG. 5F shows microscopy images illustrating that microfluidic device-mPLTs are ultrastructurally similar to mouse blood PLTs and contain a cortical MT coil, open canalicular system, dense tubular system, mitochondria, and characteristic secretory granules, in accordance with the present invention.
Figure 5G:
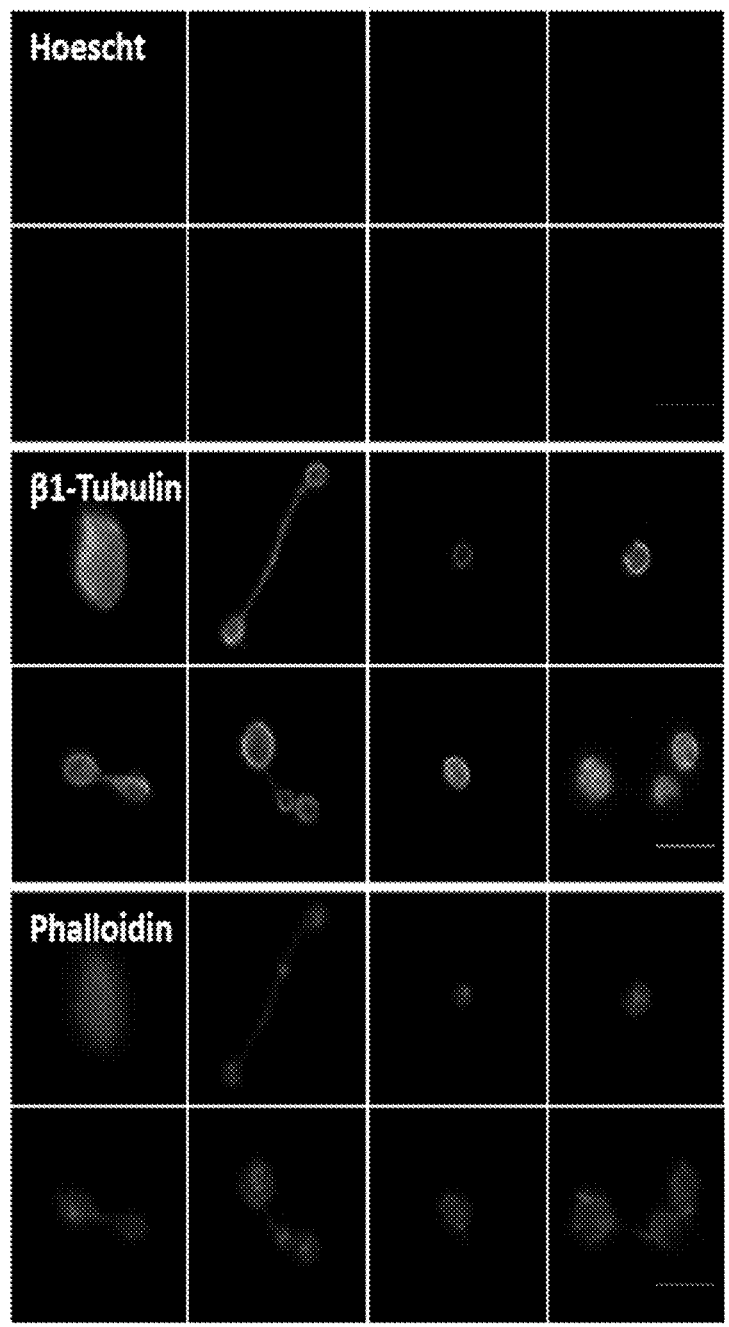
FIG. 5G shows microscopy images illustrating that microfluidic device-mPLTs and PLT intermediates are morphologically similar to mouse blood PLTs and display comparable MT and actin expression, in accordance with the present invention.

Resting PLTs contain characteristic invaginations of the surface membrane that form the open canalicular system, a closed channel network of residual endoplasmic reticulum that form the dense tubular system, organelles, specialized secretory granules, and will flatten/spread on contact activation with glass. Microfluidic device-generated PLTs were ultrastructurally indistinguishable from mouse blood PLTs by thin-section transmission electron; and contained a cortical MT coil, open canalicular system, dense tubular system, mitochondria, alpha- and dense-granules (as shown in FIG. 5F). Microfluidic device-generated PLTs and PLT intermediates displayed comparable MT and actin organization to mouse blood PLTs by immunofluorescence microscopy (as shown in FIG. 5G), and spread normally on contact-activation with glass, forming both filpodia and lamellipodia.

Application of the Microfluidic Device to Human PLT Production

Figure 6A:
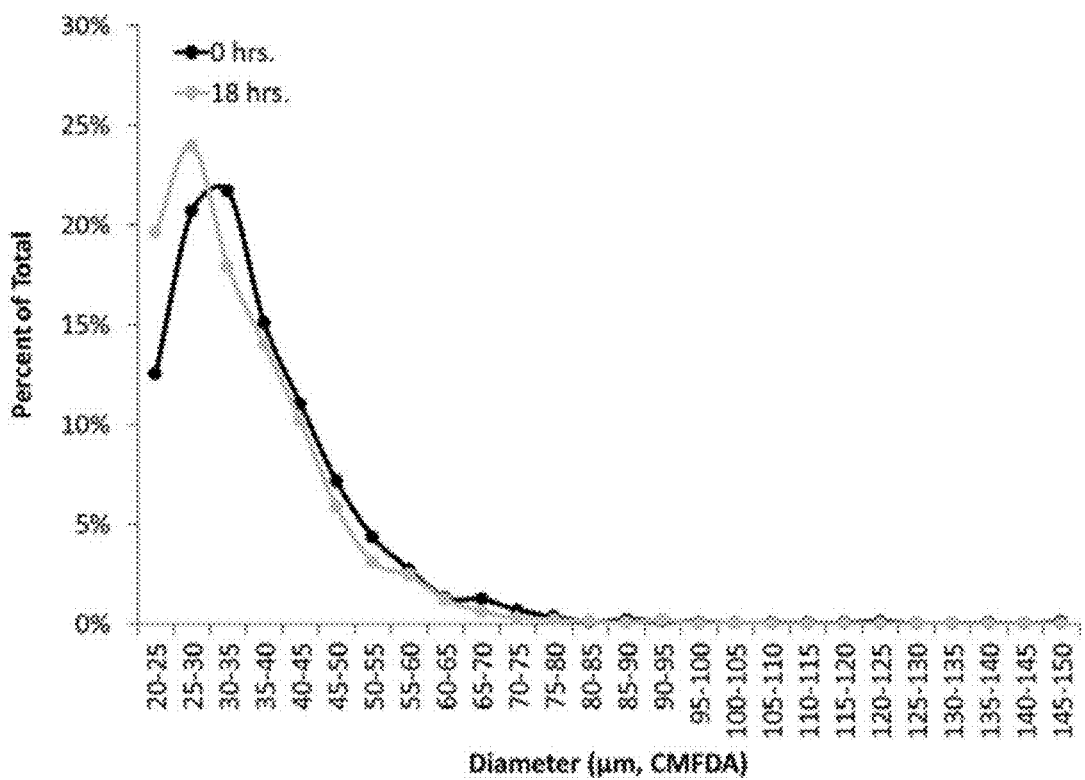
FIG. 6A is a graphical depiction illustrating that microfluidic device-derived hiPSC-PLTs manifest structural and functional properties of blood PLTs, where hiPSC-MKs reach maximal diameter (20-60 μm) on culture day 15, in accordance with the present invention
Figure 6B:
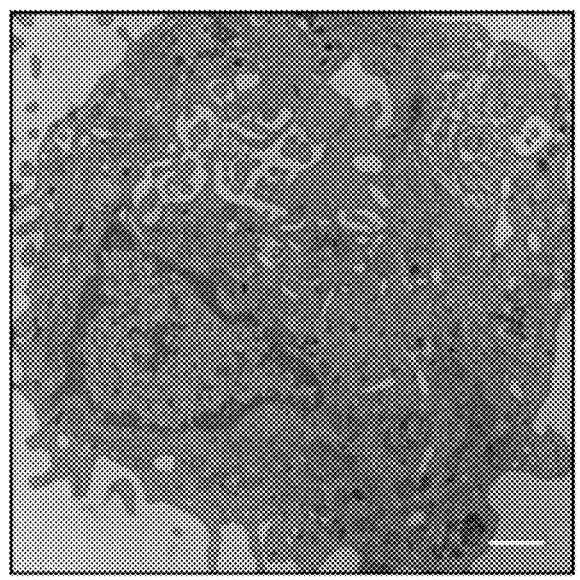
FIG. 6B shows a microscopy image illustrating that hiPSC-MKs are ultrastructurally similar to primary human MKs and contain a lobulated nuclei, invaginated membrane system, glycogen stores, organelles, and characteristic secretory granules, in accordance with the present invention.
Figure 6C:
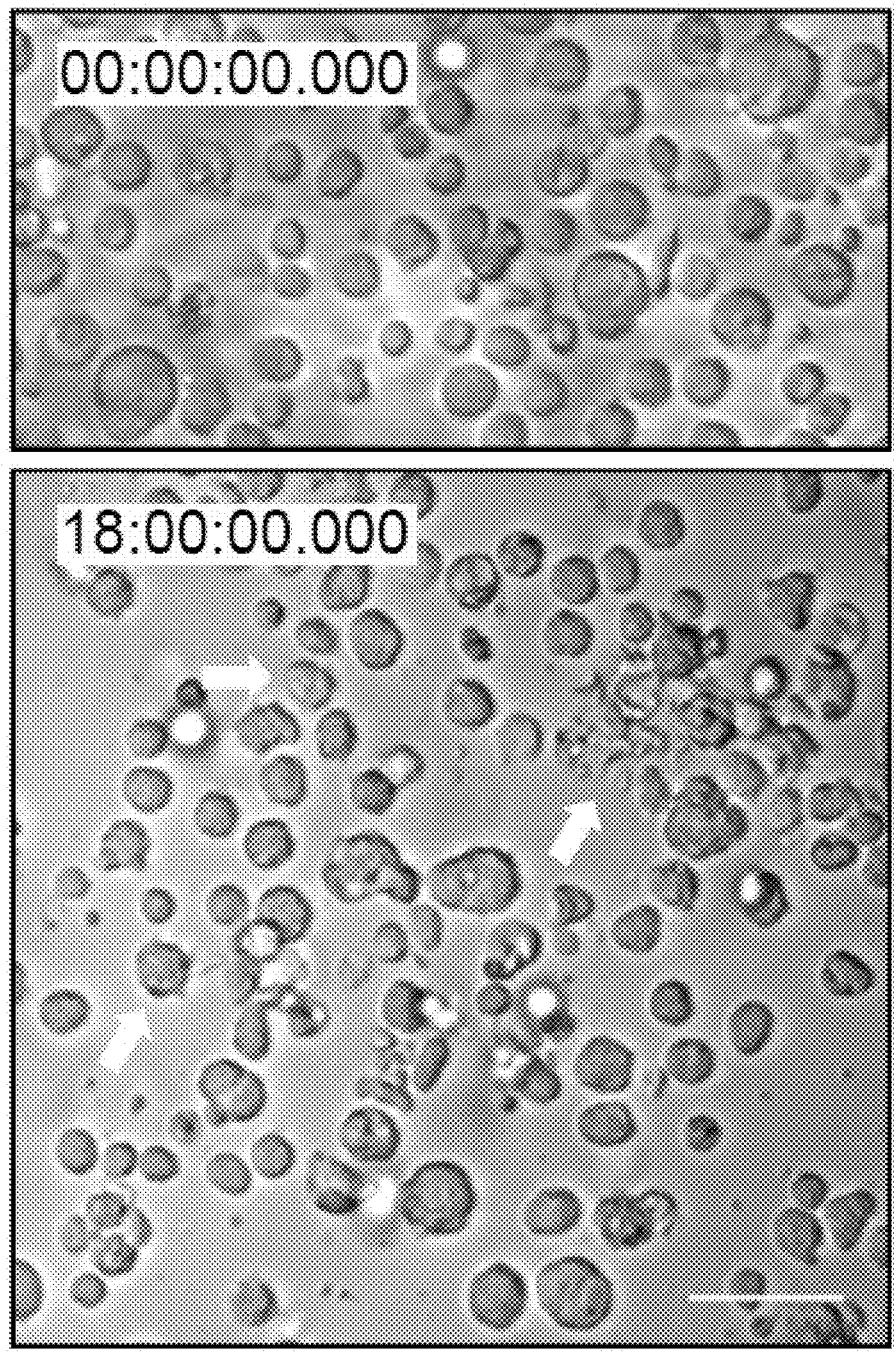
FIG. 6C shows microscopy images illustrating that hiPSC-MKs in static culture begin producing proPLTs at 6 hours post-purification, and reach maximal proPLT production at 18 hours, in accordance with the present invention.
Figure 6D:
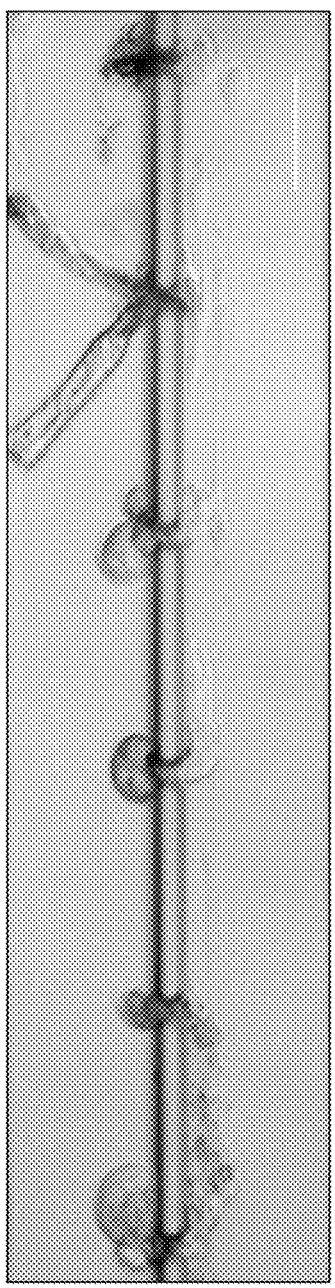
FIG. 6D shows a microscopy image illustrating that hiPSC-MKs under physiological shear (~500 s$^{-1}$) begin producing proPLTs immediately upon trapping and extend/release proPLTs within the first 2 hours of culture, in accordance with the present invention.
Figure 6F:
FIG. 6F is a graphical depiction illustrating that proPLT extension rates under physiological shear are ~19 μm/min, in accordance with the present invention.
Figure 6E:
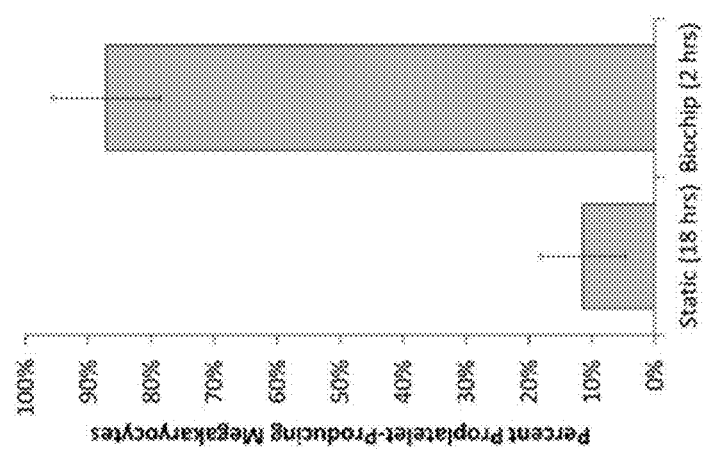
FIG. 6E is a graphical depiction illustrating that percent proPLT-producing hiPSC-MKs under physiological shear are increased significantly over static cultures, in accordance with the present invention.

To generate human PLTs, mFLC-MK in our microfluidic device were replaced with hiPSC-derived MK, which provide a virtually unlimited source of MKs for infusion. hiPSC-MKs were isolated on culture day 15, once they had reached maximal diameter of 20-60 μm (shown in FIG. 6A), and were ultrastructurally similar to primary human MKs (shown in FIG. 6B). In static culture, hiPSC-MKs began producing proPLTs at 6 hours post-isolation, and reached maximal proPLT production at 18 hours (shown in FIG. 6C). By comparison, hiPSC-MKs under physiological shear (about 500 $s^{-1}$) began producing proPLTs immediately upon trapping, and extended/released proPLTs within the first 2 hours of culture (shown in FIG. 6D). The percent proPLT-producing hiPSC-MKs under shear were increased significantly over static cultures (~10%) to roughly 90% (as shown in FIG. 6E).

ProPLT extension rates were slightly lower than mFLC-MK controls (~19 μm/min versus 30 μm/min) (shown in FIG. 6F) and more closely approximated physiological controls. Microfluidic device-generated PLTs displayed forward and side scatter, and surface biomarker expression characteristic of human blood PLTs, were ultrastructurally indistinguishable from human blood PLTs by thin-section transmission electron (shown in FIG. 6G), displaying comparable MT and actin expression to human blood PLTs by immunofluorescence microscopy (shown in FIG. 6H), spreading normally on contact-activation with glass, and forming both filpodia and lamellipodia (shown in FIG. 6I). Taken together these data demonstrate that hiPSC-MKs can be applied to our biomimetic microfluidic device to generate potentially unlimited numbers of functional human PLTs.

Application of the Microfluidic Device to Drug Development

Thrombocytopenia may appear suddenly and often unintentionally, potentially causing major bleeding and death. Antibody and cell-mediated autoimmune responses have been shown to cause thrombocytopenia. In addition, thrombocytopenia may also be triggered by a wide range of medications, including cancer drugs, such as dasatinib. Animal models are generally poor predictors of safety and efficacy of medications in humans, and clinical studies are time-consuming, expensive, and potentially harmful. Microfluidic devices designed to mimic human BM represent an area of innovation of major clinical importance, offering an efficient and realistic platform to investigate the effects of a variety of medications upon BM and MK biology.

PLT survival and clearance rates are usually measured through infusion studies using flow cytometry. Quantification of the rate and extent of proPLT production, however, is not amenable to this approach, and requires direct visualization to establish at what stage thrombocytopoiesis is affected. By contrast, the application of microfluidic devices offers a great platform to study drug effects on PLT production, one that may facilitate the identification of new regulators of PLT production and elucidate the mechanism of clinically significant drug-induced thrombocytopenias.

Figure 7:
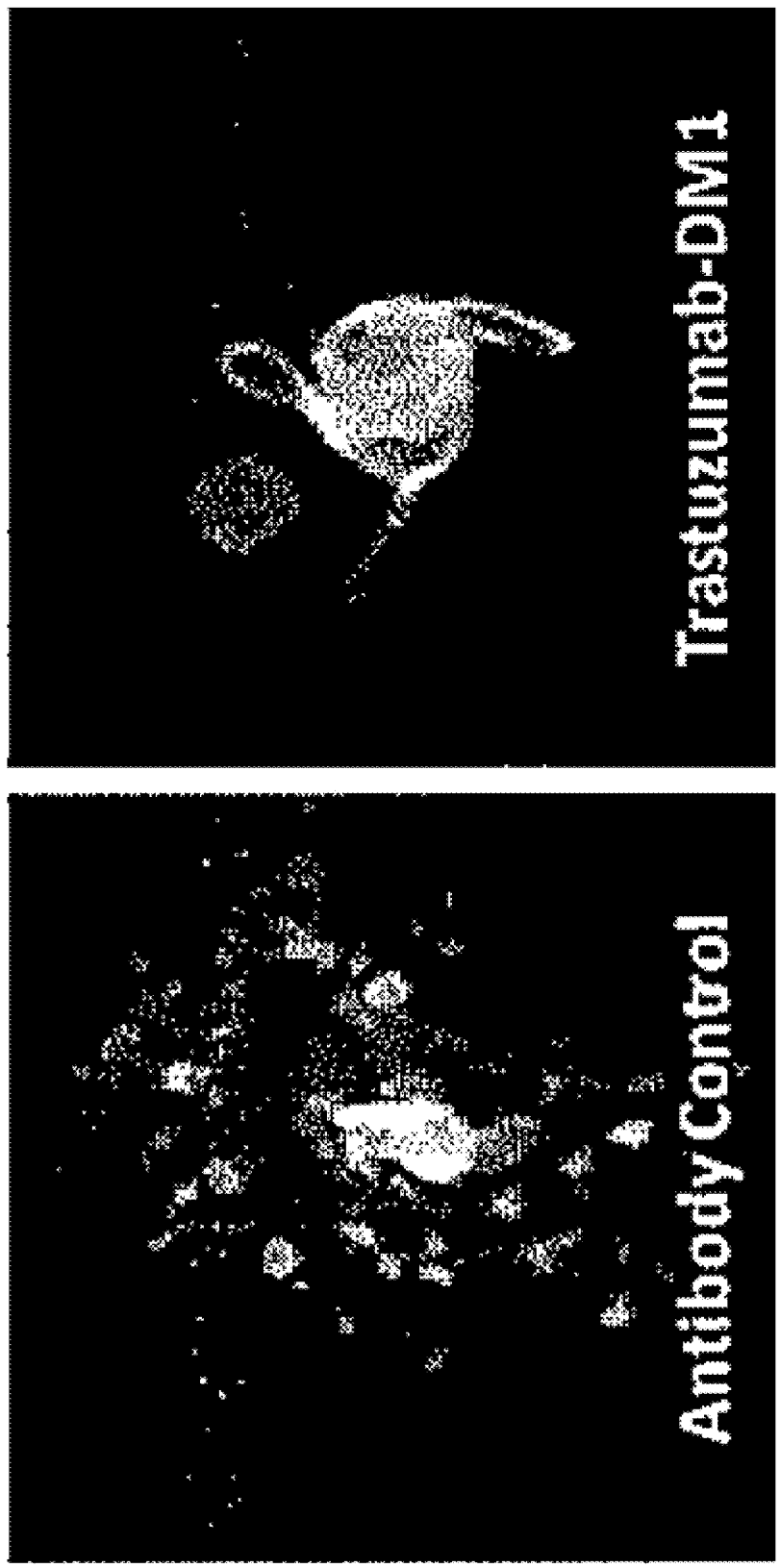
FIG. 7 shows a live-cell microscopy image illustrating that T-DM1 inhibits MK differentiation and disrupts proPLT formation by inducing abnormal tubulin organization, accordance with the present invention.

As proof of concept, high-content live-cell microscopy was employed to identify the express GFP·PI tubulin (live-cell microscopy) mechanism by which trastuzumab emtansine (T-DM1), an antibodydrug conjugate currently in clinical development for breast cancer, affects PL T production. These studies revealed that T-DM1 inhibits MK differentiation, and disrupts proPLT formation by inducing abnormal tubulin organization (as shown in FIG. 7). Defining the pathways by which therapeutics such as T-DM1 affect MK maturation and proPLT production may yield strategies to manage drug-induced thrombocytopenias and regulate PLT production in vivo.

The approach of the present invention capitalizes on a highly novel microfluidic design to recapitulate human BM and blood vessel physiology ex vivo, and generate an alternative source of functional human PLTs for infusion. While clinically desirable to meet growing transfusion needs and obviate risks currently associated with platelet procurement and storage, 2 major quantitative roadblocks have thus far persisted in the development of donor-independent PLTs for therapeutic use: (1) generating sufficient numbers (~3× $10^8$) of human MKs to support the production of one PLT transfusion unit (~3×$10^{11}$ PLTs), and (2) generating physiological numbers of functional human PLTs (~$10^3$-$10^4$) per MK. The development of human embryonic stem cell cultures (hESC), and more recently, human induced pluripotent stem cell cultures (hiPSC), offer a potentially unlimited source of progenitor cells that can be differentiated into human MKs in vitro to address the first quantitative roadblock. Indeed, because PLTs are anucleate, PLT microfluidic device-derived units could be irradiated prior to infusion, addressing concerns that cellular products derived from hESC or hiPSCs could be oncogenic or teratogenic.

Attempts to study the environmental drivers of PLT production have been constrained by reductionist approaches, and a major limitation of 2D liquid cultures has been their inability to account for 3D BM composition and stiffness, directionality of proPLT extension, and proximity to venous endothelium. Likewise, while proPLT-producing MKs entering sinusoidal blood vessels experience wall shear rates of 500 to 2500 $s^{-1}$, attempts to model vascular flow by perfusing MKs over ECM-coated glass slides have selected for immobilized/adhered MKs, and have been unable to discriminate ECM-contact activation from shear. Alternatively, released proPLTs have been centripetally agitated in an incubator shaker, which does not recapitulate laminar shear flow in BM blood vessels, does not provide precise control of vascular shear rates, and is not amenable to high-resolution live-cell microscopy. Nonetheless, despite these limitations, exposure of MKs to high shear rates (1800 s$^{-1}$) accelerated proPLT production, and proPLTs cultured in the absence of shear released significantly fewer PLTs than those maintained at fluid shear stresses of ~0.5 Pa for 2 hours. Moreover, recent advances in multiphoton intravital microscopy have provided increasing resolution of proPLT production in vivo and confirmed the importance of vascular flow on proPLT extension and PLT release. While these studies have provided physiologically accurate examples of in vivo proPLT production, poor resolution and limited control of the microenvironment has prohibited detailed study of how the BM microenvironment contributes to PLT release.

Mounting evidence that cell-cell contacts, extracellular matrix (ECM) composition and stiffness, vascular shear rates, pO2/pH, soluble factor interactions, and temperature contribute to proPLT formation and PLT release have suggested that recapitulating BM and blood vessel microenvironments within a 3D microfluidic culture system is necessary to achieve clinically significant numbers of functional human PLTs. Indeed, modular 3D knitted polyester scaffolds have been applied under continuous fluid flow to produce up to $6 \times 10^6$ PLTs/day from $1 \times 10^6$ CD34+ human cord blood cells in culture. While suggestive that clinically useful numbers of culture-derived human PLTs are attainable, 3D perfusion bioreactors have not accurately reproduced the complex structure and fluid characteristics of the BM microenvironment, and their closed modular design has prevented direct visualization of proPLT production, offering little insight into the mechanism of PLT release. Alternatively, 3D PDMS biochips adjacent ECM-coated silk-based tubes have been proposed to reproduce BM sinusoids and study MK differentiation and PLT production in vitro. While capable of recapitulating MK migration during maturation, this design is not amenable to high resolution live-cell microscopy, and does not reproduce endothelial cell contacts necessary to drive MK differentiation.

By comparison, the microfluidic device design of the present invention offers the complete package, allowing significant improvement in time to PLT release and an increased total PLT yield. Also, application of vascular shear rates within the microfluidic device induces proPLT production, and reproduces physiological proPLT extension and release. Furthermore, MKs are capable of squeezing through small gaps to enter the circulation and releasing prePLT intermediates under physiological flow conditions. The product resulting from continuous perfusion of MKs in the microfluidic device of the present invention approached physiological PLT concentrations, and manifested both structural and functional properties of blood PLTs. Finally, PLT microfluidic devices could be applied to human MK cultures to produce functional human PLTs. Although PLT yield per MK fell short of theoretical estimates, the observation that MK cultures routinely released large MK fragments (prePLTs, proPLTs) as well as MK themselves into the effluent channel, suggests that actual PLT numbers may depend on the further differentiation of PLT intermediates into PLTs in supportive microenvironments such as the lung or circulating blood. Indeed, when mFLC-derived proPLTs were infused into mice, these were rapidly converted into PLTs over a period of 12-24 hours. Interestingly, while CMFDA-labeled PLTs in this study were readily detected in the blood, larger prePLT intermediates were not, suggesting that they may be trapping in a microcirculation of the lung. Likewise, when mFLC and BM-derived MKs were infused into mice they almost exclusively localized to the lungs and released PLTs within the first two hours. In both cases, it is almost certain that vascular shear rates, soluble factor interactions in the blood, and endothelial cell contacts regulate this process, and examining how local microenvironments in these tissues contribute to terminal PLT production warrant further investigation.

By combining the major elements of BM physiology including 3D ECM composition and stiffness, cell-cell contacts, vascular shear rates, pO2/pH, soluble factor interactions, and temperature within a single microfluidic system, the approach of the present invention offers unprecedented control of ex vivo microenvironments and a biomimetic platform for drug development. Moreover, support of high-resolution live-cell microscopy permits direct visualization of cells during culture and provides a window into poorly characterized physiological processes. Lastly, the microfluidic device design can be easily scaled by mirroring effluent channels on either side of a central channel, elongating the device to support greater numbers of columns, and positioning multiple units in parallel within a larger microfluidic device matrix. Continuous harvesting of hiPSC-MKs in longer devices may result in clinically significant numbers of PLTs to perform, for example, traditional aggregometry tests of PLT function, and in vivo xeno-transfusion studies in immune-suppressed mice to measure increases in PLT counts, which require roughly $10^8$ PLTs per study.

In summary, the present invention has demonstrated a system and method to recapitulate human BM and sinusoidal blood vessel microenvironments for generating human platelets in an approach amenable to high resolution imaging. The biomimetic microfluidic system may be fabricated using PDMS bonded to glass in a configuration that includes microfluidic channels separated by a series of columns. The channels can be selectively coated with ECM and human endothelial cells to simulate realistic physiological conditions. Round or proPLT-producing MKs infused along one channel can sequentially become trapped between the columns, and extend platelet-producing proplatelets into the other channel. Stimulated by controllable physiological shear rates and regulated microenvironments, the released PLTs entering the fluid stream can be collected from the effluent, and the process may be visualized by high-resolution live-cell microscopy.

The various configurations presented above are merely examples and are in no way meant to limit the scope of this disclosure. Variations of the configurations described herein will be apparent to persons of ordinary skill in the art, such variations being within the intended scope of the present application. In particular, features from one or more of the above-described configurations may be selected to create alternative configurations comprised of a sub-combination of features that may not be explicitly described above. In addition, features from one or more of the above-described configurations may be selected and combined to create alternative configurations comprised of a combination of features which may not be explicitly described above. Features suitable for such combinations and sub-combinations would be readily apparent to persons skilled in the art upon review of the present application as a whole. The subject matter described herein and in the recited claims intends to cover and embrace all suitable changes in technology.

The invention claimed is:

1. A biomimetic microfluidic system comprising:
   a first channel extending from a first input to a first output along a longitudinal dimension, the first channel configured to receive at least one first biological composition at a first channel flow rate, the at least one first biological composition comprising a biological source material capable of producing target biological substances;

a second channel substantially parallel to the first channel and extending from a second input to a second output along the longitudinal dimension, the second channel configured to selectively receive at least one second biological composition at a second channel flow rate; and a separation barrier between the first channel and the second channel, the separation barrier having a plurality of microchannels forming a fluid communication path between the first and second channels, wherein the plurality of microchannels are sized to selectively capture the biological source material, wherein the first channel flow rate and the second channel flow rate are configured to selectively capture the biological source material at the plurality of microchannels and to create a differential between the first and second channels configured to generate physiological shear rates along the second channel that induce the captured biological source material to produce the target biological substances.

2. The system of claim 1, wherein the separation barrier is at least one of a film, a series of columns, membrane, or a mesh arranged between the first and second channels.

3. The system of claim 2, wherein the plurality of microchannels are formed as at least one of pores, gaps, or slits extending between the first channel and the second channel.

4. The system of claim 1, wherein the biological source material includes megakaryocytes and the target biological substances include platelets.

5. The system of claim 1, wherein the at least one first and the at least one second biological compositions include at least one of a semi-solid, a solid, a liquid, or a collection of cells.

6. The system of claim 1, wherein the physiological shear rates are generated to be within a range between $100\ s^{-1}$ and $10{,}500\ s^{-1}$.

7. The system of claim 1, wherein the physiological shear rates are generated to be within a range between $500\ s^{-1}$ and $2{,}500\ s^{-1}$ to induce a production of a plurality of platelets.

8. The system of claim 1, wherein the physiological shear rates are controlled by at least one of the first channel flow rate, the second channel flow rate, the longitudinal dimension, a transverse dimension of the first channel, a transverse dimension of the second channel, the at least one first biological composition, or the at least one second biological composition.

9. The system of claim 8, wherein the transverse dimensions of the first and second channels are between 100 micrometers and 3,000 micrometers.

10. The system of claim 1, wherein the system further comprises a first flow filter positioned upstream from the first input, and a second flow filter positioned upstream from the second input, wherein upstream is defined relative to a direction of flow for the at least one first biological composition and the at least one second biological composition.

11. The system of claim 10, wherein the system further comprises a first flow resistor positioned between the first input and the first flow filter, and a second flow resistor positioned between the second input and the second flow filter.

12. The system of claim 1, wherein the longitudinal dimension is between 1000 micrometers and 30,000 micrometers.

13. The system of claim 1, wherein the plurality of microchannels are sized between 0.1 micrometers and 20 micrometers.

14. The system of claim 1, further comprising a substrate, wherein the first channel and the second channel are formed in the substrate.

15. A biomimetic microfluidic system comprising:
one or more biomimetic microfluidic devices, wherein the one or more biomimetic microfluidic devices comprise:
a first channel extending from a first input to a first output along a longitudinal dimension, the first channel configured to selectively receive at least one first biological composition at a first channel flow rate, the at least one first biological composition including a biological source material capable of producing target biological substances;
a second channel substantially parallel to the first channel and extending from a second input to a second output along the longitudinal dimension, the second channel configured to selectively receive at least one second biological composition at a second channel flow rate;
a separation barrier between the first channel and the second channel, the separation barrier having a plurality of microchannels forming a fluid communication path between the first and second channels, wherein the plurality of microchannels are sized to selectively capture the biological source material,
wherein the first channel flow rate and the second channel flow rate are configured to selectively capture the biological source material at the plurality of microchannels and to create a differential between the first and second channels configured to generate physiological shear rates along the second channel that induce the captured biological source material to produce the target biological substances.

16. The system of claim 15, wherein the one or more biomimetic microfluidic devices comprise a plurality of biomimetic microfluidic devices in parallel.

17. The system of claim 16, wherein the one or more biomimetic microfluidic devices further comprise a substrate, wherein the first channel and the second channel are formed in the substrate.

18. The system of claim 16, wherein the separation barrier is at least one of a film, a series of columns, membrane, or a mesh arranged between the first and second channels.

19. The system of claim 16, wherein the plurality of microchannels are formed as at least one of pores, gaps, or slits extending between the first channel and the second channel.

20. The system of claim 16, wherein the biological source material includes megakaryocytes and the target biological substances include platelets.

* * * * *